(12) United States Patent
Sutton et al.

(10) Patent No.: US 7,728,977 B2
(45) Date of Patent: Jun. 1, 2010

(54) OPTICAL GAS DETECTION

(75) Inventors: Stephen N. Sutton, Blandford Forum (GB); Rodney Royston Watts, Wimbourne (GB); Michael Proctor, Wiesendangen (CH)

(73) Assignee: Honeywell Analytics AG, Uster (CH)

( * ) Notice: Subject to any disclaimer, the term of this patent is extended or adjusted under 35 U.S.C. 154(b) by 315 days.

(21) Appl. No.: 11/721,070

(22) PCT Filed: Dec. 16, 2005

(86) PCT No.: PCT/GB2005/004870
§ 371 (c)(1),
(2), (4) Date: Oct. 5, 2007

(87) PCT Pub. No.: WO2006/064256
PCT Pub. Date: Jun. 22, 2006

(65) Prior Publication Data
US 2009/0231588 A1  Sep. 17, 2009

(30) Foreign Application Priority Data

| Dec. 17, 2004 | (EP) | ................................. 04257885 |
| Dec. 17, 2004 | (EP) | ................................. 04257886 |
| Dec. 17, 2004 | (EP) | ................................. 04257887 |
| Dec. 17, 2004 | (EP) | ................................. 04257888 |
| Dec. 17, 2004 | (EP) | ................................. 04257889 |
| Dec. 17, 2004 | (EP) | ................................. 04257890 |
| Dec. 17, 2004 | (EP) | ................................. 04257898 |
| Dec. 17, 2004 | (EP) | ................................. 04257899 |
| Dec. 20, 2004 | (EP) | ................................. 04257895 |

(51) Int. Cl.
*G01N 21/00* (2006.01)

(52) U.S. Cl. .................................................... 356/437

(58) Field of Classification Search .......... 356/432–444
See application file for complete search history.

(56) References Cited

U.S. PATENT DOCUMENTS 3,662,171 A * 5/1972 Brengman et al. .......... 250/342
(Continued)

FOREIGN PATENT DOCUMENTS

GB    2 353 591 A    2/2001

(Continued)

OTHER PUBLICATIONS

PCT International Searching Authority, EPO, Mason, W., International Search Report, mailed May 16, 2006, 6 pages.
Canadian Search Report, dated Nov. 5, 2009 corresponding to Canadian application No. 2,590,216.

*Primary Examiner*—Gregory J Toatley, Jr.
*Assistant Examiner*—Jarreas C Underwood
(74) *Attorney, Agent, or Firm*—Husch Blackwell Sanders Welsh & Katz

(57) ABSTRACT

The present invention provides a transmitter unit for an open path gas detector for detecting a target gas and comprises: a radiation transmitter, e.g. a tuneable laser diode, capable of emitting radiation at a wavelength absorbed by the target gas, and a radiation deflector, having a deflecting part and a non-deflecting part, e.g. a mirror having a non-reflective part. The deflecting part and the non-deflecting part are located in the path of the radiation emitted by the transmitter and the non-deflecting part does not deflect the said radiation emitted by the transmitter or does so to a different extent than the deflecting part. In this way, the beam has a core in shadow that can be used to align the beam with a receiver unit. The radiation deflector is preferably a mirror having a reflective surface for reflecting radiation emitted by the transmitter and a non-reflective part that does not reflect the said radiation emitted by the transmitter or does so to a lesser extent that the reflecting surface. The non-reflective part is preferably transparent so that it allows radiation to pass through it, which can be used to measure the wavelength of the transmitter and, if necessary correct it.

16 Claims, 18 Drawing Sheets

U.S. PATENT DOCUMENTS

| | | | |
|---|---|---|---|
| 4,452,532 A * | 6/1984 | Grollimund et al. | 356/121 |
| 5,420,723 A | 5/1995 | Galle | 359/857 |
| 5,591,975 A * | 1/1997 | Jack et al. | 250/338.5 |
| 5,767,976 A * | 6/1998 | Ankerhold et al. | 356/437 |
| 6,351,309 B1 | 2/2002 | Bomse et al. | 356/437 |
| 6,538,728 B1 * | 3/2003 | Stolle et al. | 356/437 |
| 7,030,991 B1 * | 4/2006 | Kampe et al. | 356/454 |
| 2001/0025927 A1 | 10/2001 | Ankerhold | 250/338.5 |

FOREIGN PATENT DOCUMENTS

| | | |
|---|---|---|
| GB | 2 373 045 A | 11/2002 |
| WO | WO 01/81878 A2 | 1/2001 |

* cited by examiner

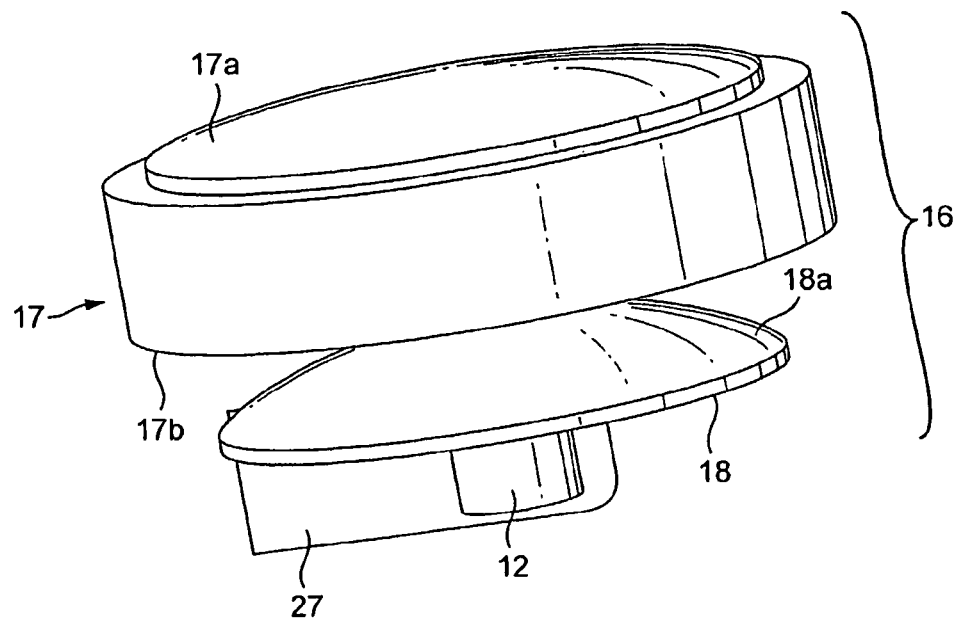
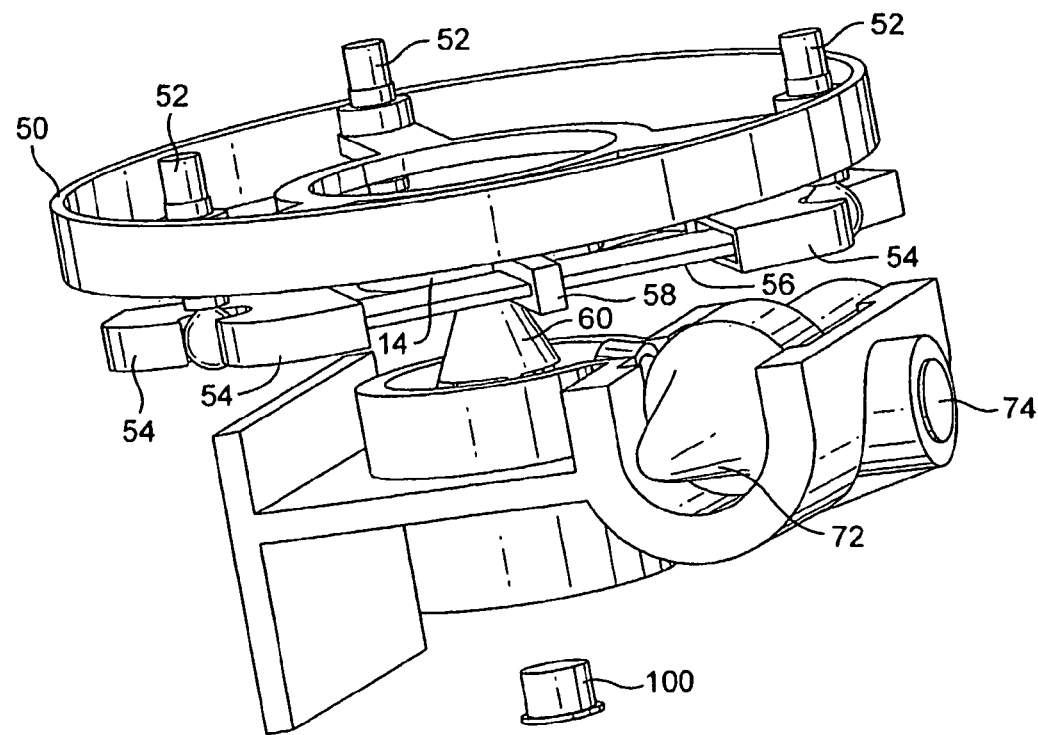
FIG. 4

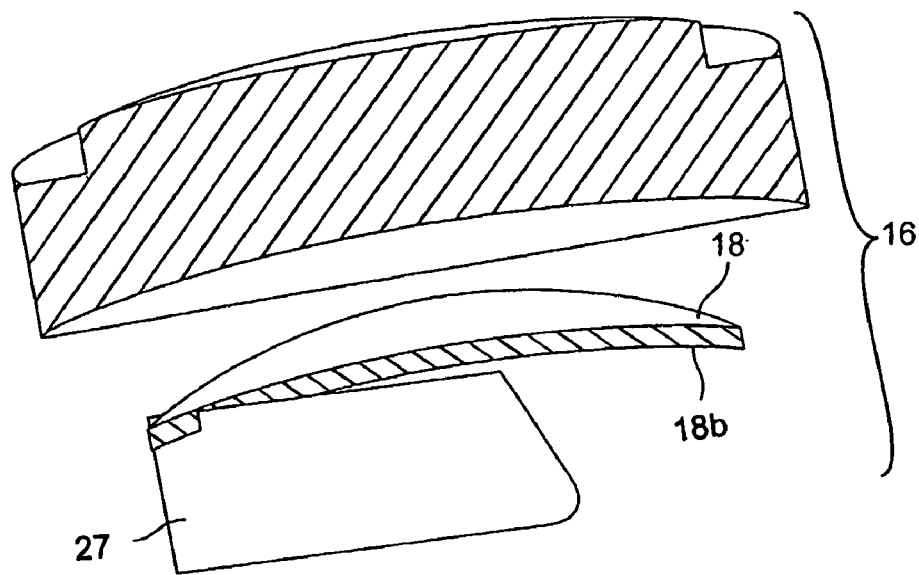
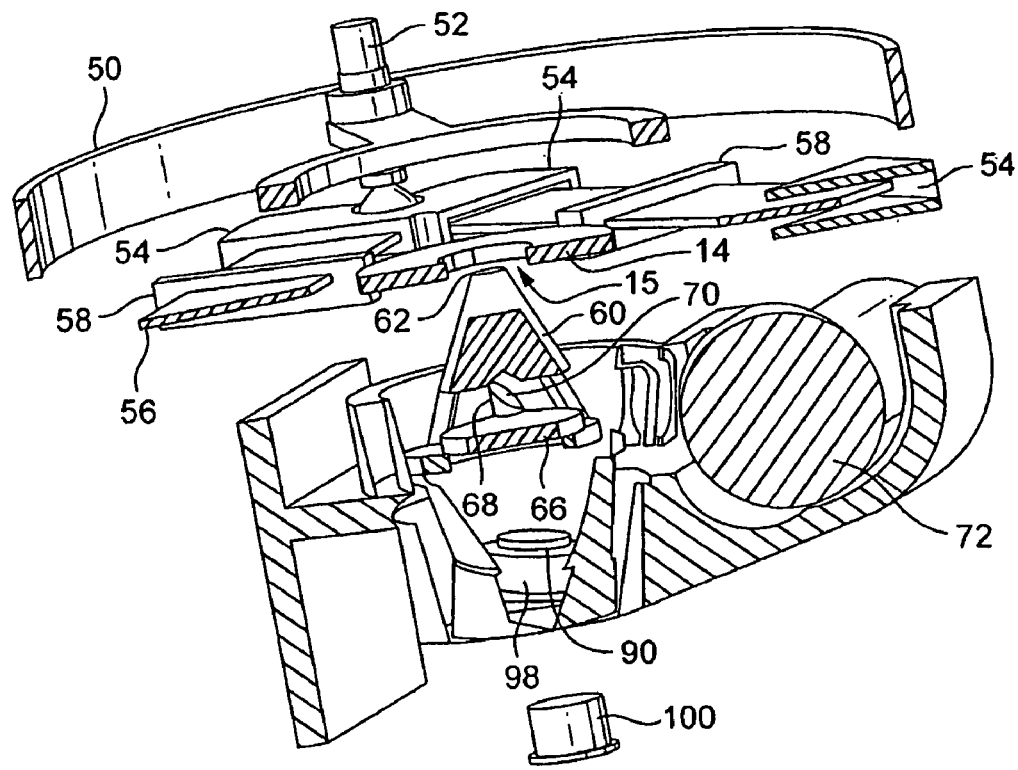
FIG. 5

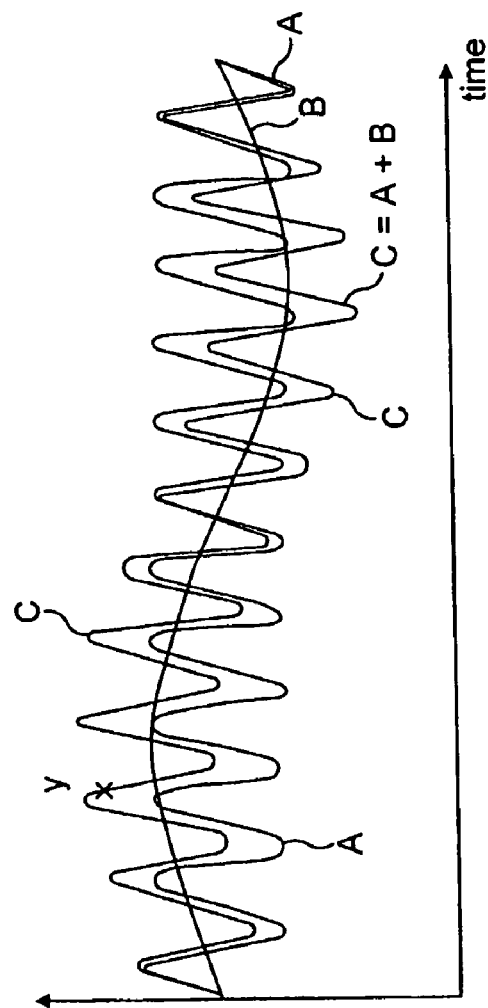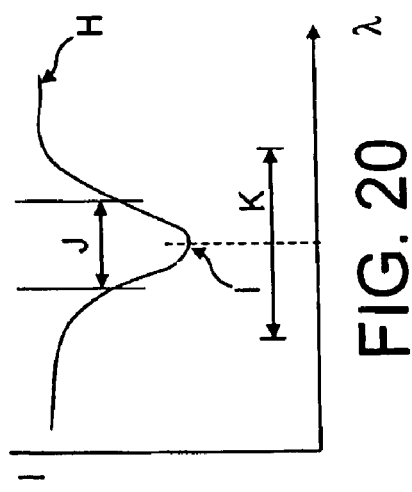

OPTICAL GAS DETECTION

The present application is a U.S national stage application of International Application No. PCT/GB2005/004870, filed Dec. 16, 2005, which International application was published on Jun. 22, 2006, under International Publication No. WO 2006/064256 A1. The International application claims priority of European Application No. 04257886.4, filed Dec. 17, 2004, EP Application No. 04257887.2, filed Dec. 17, 2004, EP Application No. 04257898.9, filed Dec. 17, 2004, EP Application No. 04257890.6, filed Dec. 17, 2004, EP Application No. 04257885.6, filed Dec. 17, 2004, EP Application No. 04257895.5, filed Dec. 17, 2004, EP Application No. 04257888.0, filed Dec. 17, 2004, EP Application No. 04257899.7, filed Dec. 17, 2004, and EP Application No. 04257889.8, filed Dec. 17, 2004 and this application also claims the benefit of the date of the EP applications, that is Dec. 17, 2004.

INDUSTRIAL FIELD

The present invention relates to the infrared detection of gases, which term also includes vapours. It especially concerns open path gas detectors that are used to detect gases and that include a transmitter unit that transmits a beam of radiation across a path in a space being monitored and a detecting unit that detects the radiation that has passed across the space. The term "open path gas detector" is used to cover detectors irrespective of the length of the path and irrespective of whether the path is open to atmospheric conditions and/or is enclosed.

BACKGROUND ART

The use of non-dispersive infrared spectroscopy to detect hydrocarbon gases is well established. It essentially involves transmitting infrared radiation along a path in an area being monitored; the wavelength of the infrared radiation is chosen so that it is absorbed by the gas of interest (hereafter called the "target gas") but not substantially absorbed by other gases in the atmosphere of the area being monitored. If monitoring out-of-doors, the wavelength should ideally not be absorbed by liquid or gaseous water (e.g. in the form of humidity, condensation, fog, rain or spray). The intensity of the radiation that has passed along the path in the area being monitored is measured and the attenuation in the intensity of the radiation gives a measure of the amount of target gas in the monitored area.

However, factors other than absorption by the target gas also attenuate the infrared radiation, including obscuration of the detecting beam, atmospheric scattering of the radiation, contamination of the surfaces, e.g. by dirt or condensation, and ageing of components. The reliability of infrared gas detectors is significantly improved by the use of a reference; such a reference is usually infrared radiation at a different wavelength which ideally is a wavelength at which the target gas does not exhibit significant absorption. Radiation at more than one reference wavelength may be used; likewise more than one sample wavelength may be used. The ratio between the signal obtained at the wavelength(s) where the target gas does absorb (the "sample" wavelength(s)) and the signal obtained at the wavelength(s) where the target gas does not significantly absorb (the "reference" wavelength(s)) compensates for the attenuation caused by environmental conditions since ideally the signal at the reference wavelength(s) and the signal at the sample wavelength(s) will both be affected to the same extent by effects (other than the presence of target gas) that attenuate the radiation.

It is known to monitor the presence of toxic gases in an atmosphere using point gas detectors, which can be electrochemical or optical (the term "toxic" gas in the context of the present specification means a gas or vapour other than oxygen and nitrogen, such as hydrogen sulphide, hydrogen fluoride, ammonia, sulphur dioxide, carbon dioxide and carbon monoxide). The provision of point gas detectors gives rise to problems when monitoring a large area since the placing of numerous detectors throughout the area is expensive. Furthermore, if the build up of target gas takes place between detectors, it will not be detected. Open path gas detectors with a path length in excess of 1 meter, typically at least 10 m, allow a much larger area to be monitored by a single instrument.

The use of open path gas detectors has been made more attractive by the ready availability at a reasonable price of tuneable diode lasers, which can be tuned to a very narrow wavelength to detect characteristic absorbency wavelengths of target toxic gases. However, the levels of toxic gas that must be detected are low, typically 5 ppm (parts per million) and can be lower, e.g. 1 ppm. At such low levels, the noise in the detector can be greater than the signal of the target gas, making it very difficult to detect such low levels of toxic target gases. In addition, the signal can become indiscernible due to drift in electronic or optical components over time, variations in temperature and/or atmospheric conditions, etc. In addition, the use of coherent laser irradiation from a tuneable laser diode can give rise to interference fringes where the variation in the intensity of the radiation between the bright and dark fringes far exceeds the signal arising from the presence of low levels of the target gas.

Accordingly, no low cost reliable open path gas detector for toxic gases measuring target gas levels as low as 10 ppm has hitherto been possible.

GB-2353591 describes an open path gas detector that uses a tuneable laser diode as the radiation source directing a beam across a measuring path to a radiation detector in order to detect target gas within the path. The laser diode transmits radiation in a very narrow line width, much narrower than the absorption peak of a target gas. In such a known system, the wavelength of the laser diode is scanned across the absorption band of the target gas with a frequency f; the absorption band of the target gas is shown by line B in FIG. 1. In the process of scanning, the intensity of the transmitted laser radiation also varies with a frequency f; a graph of the variation of intensity with wavelength is shown as plot A in FIG. 1. The radiation transmitted is sensed by a detector that produces a signal proportional to the intensity of the radiation incident on it. A plot of intensity against time is not shown but is sinusoidal. If the atmosphere contains no target gas, the variation of the intensity of the radiation is given by plot A of FIG. 1 and the signal from the detector has a frequency that is the same as the scan frequency f. However, if there is target gas in the atmosphere, it will absorb the radiation, thereby attenuating the radiation reaching the detector. The resulting plot of the intensity of the radiation detected is a combination of curves A and B, as shown in FIG. 2. As will be appreciated, a plot of intensity against time has an additional frequency component of 2f.

The greater the amplitude of the 2f component, the greater amount of target gas there is in the measuring path. The 2f component (and higher harmonic components) of the signal can be determined using a phase-sensitive measuring amplifier (lock-in amplifier). The effect of the target gas on the 1f component will be relatively small compared to the 2f component. Consequently, a quotient formed from the 2f component and the 1f component can give a measure of the amount of target gas in the measuring path. The 1f and 2f components will be influenced in a similar manner to numerous attenuation conditions, for example the length of the measuring path, obscuration of the detecting beam, atmospheric scattering etc. Therefore, the 2f:1f quotient provides a measure of the amount of target gas in the measuring path.

Various elaborations on this basic technique are also known, for example it is possible to vary the median wavelength of the laser diode output at a slow frequency as compared to f. This provides a number of 2f:1f quotients, which can be analysed mathematically to provide a more reliable measure of the concentration of the target gas.

To obtain the variation in wavelength necessary to scan across the gas absorption band of a target gas, the electrical current through the laser is varied and consequently the optical output power also varies. Due to the nature of laser diodes, the magnitude of the 1f component is necessarily large. The magnitude of the 2f component is a function of the gas absorption and will be small for low levels of toxic gas. The 2f:1f quotients are therefore very small, typically $10^{-4}$ to $10^{-6}$ and the small value of this quotient is a substantial disadvantage of this technique since it is difficult to measure accurately.

Electronic assemblies employed to drive the laser and implement the phase sensitive measuring amplifier cause harmonic distortion of the signals. As the 1f component of the signal propagates through these electronic assemblies, any non-linear characteristics will result in harmonics of the 1f component being generated, including a component at 2f. This additional 2f component is summed with the 2f component resulting from absorption by the target gas leading to incorrect measured target gas concentrations, which can also give rise to false alarms, leading, in some cases, to a lack of credibility in the equipment.

In GB-2353591, the median value of the scanned wavelength is controlled by a feed-back circuit, as follows. A beam splitter is provided in the laser diode beam and part of the beam is directed along the measuring path and part is directed at a detector; a cell that holds a sample of the target gas (or some other substance having a suitable known absorption characteristic) is placed in front of the detection unit and so absorbs radiation at the wavelength of the target gas. The signal from the detector will show whether or not the wavelength of radiation emitted by the diode scans the absorption band of the target gas by determining the 2f:1f quotients for this feed-back beam in the same way as for the measuring beam, as discussed above. If the wavelength of the laser diode has drifted, this will be evident from the signal from the detector and allows a correction to be applied to the laser diode to bring it back to the correct wavelength.

One disadvantage of the above arrangement is that the beam splitter provides interference fringes that can swamp the signal of the target gas when it is present at a low concentration in the measuring path, as discussed above.

It is often difficult to provide optimum alignment of the measuring path between the transmitter unit and the detector unit at opposite ends of the measuring path. GB-2353591 suggests two-way communication link between the detector unit and the transmitter unit. The transmitter unit includes steering mirrors for changing the direction of the transmitted beam; the transmitted beam is periodically scanned and the optimum direction of the beam is determined as that at which the intensity measured by the detecting unit is greatest; the communication link between the detector unit and the transmitter unit provides feedback on the optimum position of the steering mirrors to achieve alignment.

One problem with open path gas detectors is water condensation on the optics, which obscures the transmitted beam. Accordingly, the optics are maintained at a temperature above the dew point to prevent such condensation. However, the heating of the optics adds to the complication of the system and it consumes substantial quantities of energy.

DISCLOSURE OF INVENTION

The present invention is defined in the accompanying claims.

According to one aspect of the present invention, there is provided a transmitter unit for an open path gas detector for detecting a target gas comprising:

a radiation transmitter, e.g. a tuneable laser diode, capable of emitting radiation at a wavelength absorbed by the target gas, a radiation deflector, having a deflecting part and a non-deflecting part, wherein the deflector is configured such that both the deflecting part and the non-deflecting part are located in the path of the radiation emitted by the transmitter and wherein the non-deflecting part does not deflect the said radiation emitted by the transmitter or does so to a different extent than the deflecting part.

The radiation deflector is preferably a mirror having a reflective surface for reflecting radiation emitted by the transmitter, and also having a non-reflective part that does not reflect the radiation emitted by the transmitter or does so to a lesser extent than the reflecting surface.

The non-deflecting part of the radiation deflector will preferably be surrounded by a deflecting part and preferably is located in the centre of the deflecting part of the radiation deflector.

As a result of the non-deflecting part, the beam produced will incorporate a full or partial shadow that can be detected and used to align the emitted radiation with a detector.

The radiation that is incident on the non-deflecting part can be put to use by allowing it to pass through the non-deflecting part, e.g. by making it transparent or translucent or by making it as an opening or a hole. The portion of the deflector that is transparent or translucent may have a diameter of less than 3 mm, preferably less than 2 mm, e.g. about 1.5 mm. For example the radiation passing through the non-deflecting part may be used to control the wavelength of the radiation emitted by the radiation transmitter by directing at least part of it through a container that is translucent to the radiation. The container is used to contain a sample of a material that absorbs radiation in at least part of the wavelength range emitted by the transmitter and is preferably a sample of the target gas. A radiation detector is arranged to detect the radiation that has passed through the container and to generate a signal in accordance with the intensity of such radiation, which signal is fed to a controller that controls the wavelength of the radiation emitted by the radiation transmitter. The wavelength absorbed by the sample is fixed and known and is used as a basis against which the radiation from the transmitter can be assessed to maintain it within a predetermined range.

The transparent or translucent non-deflecting part may also be used to transmit radiation that does not come directly from the radiation transmitter, for example to provide a reference signal to measure the intensity of the radiation emitted by the transmitter so that allowance can be made for fluctuations in the radiation intensity during gas measurement. The transmitter unit will include optics that shape the radiation from the radiation deflector into a beam for transmission along a path. The optics will preferably include an element having a surface, which is preferably spherical, facing the radiation deflector and arranged to reflect radiation from the radiation deflector and focus it so that it passes through the non-deflecting part of the radiation deflector, where it is incident on a reference detector that generates a signal that provides a measure of the radiation emitted by the transmitter, e.g. the intensity and/or wavelength of the radiation. The reflecting surface of the optics is advantageously so shaped that it focuses the reflected radiation in the vicinity of the transparent or translucent portion of the deflector.

The radiation reflected by the lens element will include a shadow cast by the non-deflective part. The radiation passed to the sample container may be kept separate from the radiation that that is passed to the reference detector by arranging a second radiation deflector, e.g. a reflector, prism or refractive component, in the shadow so that it receives no light reflected from the lens element but does receive radiation that has passed through the non-deflective part directly from the radiation source. The second deflector deflects such radiation towards the container.

The radiation reflected by the said optics surface may be focused by a further lens onto the detector; this further lens may provide a useful support for mounting the second deflector.

A shield is preferably arranged to block radiation that is directed towards the radiation transmitter and that emanates from the side of the radiation deflector remote from the radiation transmitter. The shield blocks such radiation and reduces or prevents it from producing interference fringes with the radiation from the transmitter.

The present invention also provides an open path gas detector comprising a transmitter unit for directing a beam of radiation along a path, and a receiving unit having a detector for detecting the radiation that has traversed the path. It may also include a controller configured to detect when the beam is aligned with the receiving unit and to steer the radiation deflector. The full or partial shadow cast by the non-deflecting part of the radiation deflector can be detected by the receiving unit and used to steer the radiation deflector so that the shadow impinges on the detector.

The present invention further includes an arrangement for steering a radiation deflector, e.g. a mirror, along an optical path. In this arrangement, the radiation deflector is supported on a plurality of electromechanical elements, e.g. piezoelectric elements, whose location can be adjusted in accordance with a signal applied to them; by applying appropriate signals to the elements, the radiation deflector can be steered to direct the radiation along a desired path.

The piezoelectric elements can each be a strip having two opposed ends and a central part located between the ends. Each strip is anchored at its ends and the radiation deflector is supported on the central part of the strips. Using such an arrangement the electromechanical elements may have a resonance frequency of at least 150 Hz, such as at least 200 Hz, preferably at least 300 Hz, e.g. more than 500 Hz.

The radiation in the beam transmitted along the path preferably has a divergence of less than 0.25°, preferably less than 0.1° so as to maximise the intensity of the beam, whereas the receiver can have a relatively angular wide reception range of >±0.1°, e.g. >±0.25°, preferably >±0.5°, e.g. 1°.

The same optics that is used for shaping the gas detecting beam transmitted along the path may also be used for collecting a signal containing data regarding the detection of target gas. Thus, according to a further aspect of the present invention, there is provided an open path gas detector comprising:
 a transmitter unit having
 a radiation transmitter,
 optics configured to shape radiation emitted by the transmitter into a beam for transmission along a path, and
 a communication signal detector, a receiving unit having
 a detector configured to detect the said beam of radiation from the transmitter unit and
 a communications transmitter configured to send a data signal to the transmitter unit at a communications wavelength that is different from the wavelength transmitted by the radiation transmitter, the data signal containing data concerning the intensity of radiation detected by the detector, wherein the optics is arranged to direct the data signal towards the communications signal detector.

The radiation deflector may be an optical element configured to direct radiation emitted by the transmitter towards the optics that is capable of transmitting the communications signal at the communications wavelength to the communication signal detector, which is located behind the optical element. The optical element is preferably a reflector e.g. a mirror, that is transparent or translucent at the communications wavelength and is reflective at the wavelength transmitted by the radiation transmitter.

A lens may be located between the optics and the communications detector that focuses the communications signal from the optics onto the detector.

The intensity of radiation emitted by the transmitter can vary and, as mentioned above, a reference beam of radiation can be formed that can be used to measure the intensity of the emitted radiation so that variance in the intensity can be compensate for. According to this aspect of the present invention, there is provided a transmitter unit for an open path gas detector comprising:
 a radiation transmitter, e.g. a tuneable laser diode,
 optics configured to shape radiation from the transmitter that is incident on the optics into a beam for transmission along a path, said optics comprising at least one element having a surface facing the radiation incident on the optics (hereafter referred to as the "back surface"), the back surface, which is preferably spherical, being capable of reflecting a proportion of the radiation incident on it, and
 a reference detector that is arranged to receive radiation reflected by the back surface and to generate a signal that provides a measure of a characteristic of the radiation emitted by the transmitter, e.g. the intensity and/or wavelength of the radiation.

The optics may comprise a first lens and a second lens located between the first lens and the radiation transmitter, in which case, the back surface is preferably provided in the second lens.

A further lens system may be provided that directs the radiation reflected by the back surface onto the reference detector.

An advantage of using the back surface of the optics is that substantially all the radiation that forms the beam is incident on the back surface and so the radiation reflected by the back surface is derived from substantially the whole width of the beam and not just part of it.

The heat generated by the radiation transmitter can be used to heat the optics to reduce condensation on the optics and to remove the excess heat from the transmitter. Thus, according to a still further aspect of the present invention, there is provided a transmitter unit for an open path gas detector comprising a radiation transmitter, e.g. a tuneable laser diode transmitter, and optics arranged to shape radiation emitted by the transmitter into a beam for transmission along a path, wherein the transmitter is in thermal contact with the optics whereby heat can be transferred from the transmitter to the optics. The radiation transmitter may be bonded to the optics, e.g. with an adhesive.

The optics may comprise a first lens and a second lens located between the first lens and the radiation transmitter, in which case the radiation transmitter is in thermal contact with the first lens, which can be achieved by providing the second lens with a central through-hole such that the radiation transmitter is accommodated in the hole.

The heat loss from the radiation source will probably be insufficient to cool the radiation transmitter and so a cooler may arranged to cool it further; a sensor may also detect the temperature of the radiation transmitter and a controller may operate the cooler to keep the radiation transmitter within a predetermined temperature range.

Likewise if the heat from the radiation source is insufficient to heat the optics, a top-up heater may arranged to heat the optics further.

The present invention also provides a method of aligning the beam of radiation emitted by a transmitter with a detector, e.g. aligning a beam of radiation in an open path gas detector with a detector, the beam being transmitted along a path. The method comprises:

a) generating a beam of radiation, b) detecting, using the detector, the intensity of the radiation after it has traversed the path and producing a signal giving a measure of the intensity detected, c) steering the beam in a predetermined looped pattern around the detector at a frequency f, d) deriving a position of the detector with respect to the looped beam from the variation in the intensity of the detector signal at a frequency of f' or a harmonic of f' (e.g. 2f', 4f' etc), e) directing the beam towards the said position and optionally:

f) steering in a further looped pattern around the position of the detector derived from step d) and g) optionally repeating steps d) to f) until the beam of radiation is aligned with the detector.

Thus the beam is steered in a path around the detector and the signal from the detector is analysed to find the position of the detector within the path so that the beam can be brought into alignment with the detector. The process may be done iteratively, e.g. by using successively narrow looped paths, until alignment is achieved.

As mentioned above, the beam may be annular in cross section, having a central core in full or partial shadow and alignment of the beam may be achieved by detecting the presence of the shadow.

The amplitude of the signal from the detector at a frequency f' or a harmonic of f', where f' is the frequency at which the beam is moved around the predetermined looped pattern, can be used to provide a measure of the angular distance between a central region within the loop and the detector, e.g. the angular distance between the centre of a circular loop and the detector.

The beam may be steered in a circular or non-circular, e.g. elliptical, path; when steered in a non-circular pattern, the ratio of the amplitude of the signal at the fundamental frequency f' or a harmonic thereof, e.g. 2f', to the amplitude of the signal at a different harmonic, e.g. 4f', can provide a measure of the distance between a central region within the loop and the detector.

The phase of the variation in the intensity of the signal from the detector at frequency f' or a harmonic of f' can provide a measure of the direction of the detector with respect to a central region within the loop, e.g. the centre of a circular loop.

The present invention may work even if there are variations in the signal from the detector arising from mechanical vibration of the transmitter. The magnitude, frequency, phase and direction of the mechanical vibrations can be calculated using the same techniques as finding the correct alignment of the beam with the detector since the vibrations can be seen as one form of misalignment. The beam can then be steered so that it moves with the same magnitude and frequency as the detected vibration but with the opposite phase so as to at least partly reduce the misalignment of the beam caused by the vibration.

The magnitude and direction of the vibration may be calculated from the amplitude and the phase (respectively) of the signal at:

the vibration frequency or a harmonic thereof or a frequency that is the sum of or the difference between (a) the vibration frequency or a harmonic thereof and (b) the looped frequency f' or a harmonic thereof.

According to a further aspect of the present invention the distance between a radiation detector and a source of a beam of radiation can be detected by directing the beam in at least two different directions each having a different angular variance from a direct line between the detector and the source, measuring the change of the intensity of radiation detected by the detector at the at least two different directions and calculating the change of the intensity of the detected radiation with angular variance to give a measure of the distance between the detector and the source of the beam.

A further aspect of the present invention relates to avoidance of the problem discussed above of detecting the presence of target gas by calculating the quotient of (1) the signal at the frequency f that the laser output is scanned across wavelengths in the vicinity of an absorption band to (2) the signal at the frequency 2f, namely that a signal at 2f can arise from harmonic distortion as well as from the presence of the gas, thereby distorting the calculated gas level. According to this aspect of the invention, there is provided a method of detecting a target gas present in a space, which method comprises:

generating a composite signal containing two or more different modulation frequency components;

using the composite signal to drive an radiation source to generate radiation that changes wavelength in accordance with the composite signal;

directing the radiation across the space being monitored;

detecting the radiation that has crossed the space; and generating a detected radiation signal in accordance with the radiation detected wherein the composite signal is such that absorption of the radiation by the target gas in the space being monitored results in the detected radiation signal containing at least one frequency component that is not at the fundamental or a harmonic of one or more of the modulation frequencies of the composite signal The frequency component in the detected radiation signal generated by the presence of target gas in the space may be a frequency that is the difference between two of the modulation frequency components of the composite signal or harmonics thereof and/or a frequency that is the sum of two of the modulation frequency components of the composite signal or harmonics thereof.

The frequency of one modulation frequency component is preferably greater than 1 and is up to $10^8$ times that of the second modulation frequency component, e.g., 1.1 to 100 times, such as about 10 times.

The use of a composite signal having modulation frequency components formed by combining two or more signals having different alternating waveforms can have a different, independent advantage. By forming each signal level in the composite signal, over time, by a plurality of different combinations of signal levels of the two or more signals, it is possible to reduce the non-linearity between the generators forming the two signals and the radiation emitted by the radiation source. Thus the invention also provides a method of detecting a target gas present in a space, which method comprises:

combining two or more signals having different alternating waveforms to generate a composite signal, using the composite signal to drive an radiation source, e.g. a tuneable laser diode, to generate radiation that changes wavelength in accordance with the composite signal;

directing the radiation across the space being monitored; and detecting the radiation that has crossed the space;

wherein each signal level in the composite signal is obtained, over time, by a plurality of different combinations of signal levels of the two or more signals.

It is preferred that the composite signal is such that its average signal level is such as to cause the radiation source to generate radiation at an absorption wavelength of the target gas. The two or more signals preferably include two or more alternating waveforms and a direct current, in which case the direct current may be such as to cause the radiation source to generate radiation at the absorption wavelength of the target gas.

The present invention also relates to a transmitter unit of an open path gas detector configured to implement the above methods and an open path gas detector including such a transmitter unit.

The use of a composite signal having two or more modulation frequency components to drive the radiation source in a gas detector can be used to give a third, independent advantage. By filtering one of the frequency components out of the signal formed by detecting the radiation that has passed through a gas, errors caused by non-linearities between the input and output of electrical components used in gas detection, e.g. amplifiers or analogue-to-digital converters, can be reduced. Thus according to this aspect of the present invention there is provided a method of detecting a target gas in a space, comprising:

generating a detected radiation signal in accordance with the radiation detected;

filtering the detected radiation signal to remove at least one frequency component corresponding to one of the signals used to form the composite signal;

feeding the filtered detected radiation signal to an input of signal processor having a non-linear output, e.g. an analogue to digital converter or an amplifier;

and analysing the filtered signal output to detect absorption of the radiation directed across the space at the absorption wavelength of the target gas.

Thus the filtered detected radiation signal may be fed to an input of a signal processor that has a non-linear output, e.g. an analogue to digital converter or an amplifier, and wherein the analysing step includes analysing the filtered signal from the output to detect absorption of the radiation directed across the space at the absorption wavelength of the target gas.

The presence of the target gas in the space generates frequency components in the detected radiation signal, which may include a first frequency component that is the difference between at least two modulation frequency components of the composite signal or harmonics thereof and/or a second frequency that is the sum of at least two modulation frequency components of the composite signal or harmonics thereof.

As before, the ratio of the frequencies of the first and second modulation frequency component is greater than 1:1 and may be up to $10^8$:1, e.g. 1.1:1 to 100:1, such as about 10:1.

The present invention also relates to a receiver unit of an open path gas detector configured to implement the above method and an open path gas detector including such a receiver unit.

BRIEF DESCRIPTION OF DRAWINGS

There will now be described, by way of example only, a transmitter unit and a detector unit of an open path gas detector in accordance with the present invention, by reference to the following drawings in which:

FIG. 4 is an assembly showing the various parts of the transmitter unit of the open path gas detector;

FIG. 5 is the same as FIG. 4 except it is shown partly broken away and partly exploded;

FIG. 19 is a series of three plots, two of which are of component signals that are combined to form the signal of the third plot, which is the drive signal for the laser diode of the open path gas detector;

FIG. 20 is a plot of the absorption band of a target gas;

DESCRIPTION OF BEST MODE FOR PUTTING THE INVENTION INTO OPERATION

Figure 3:
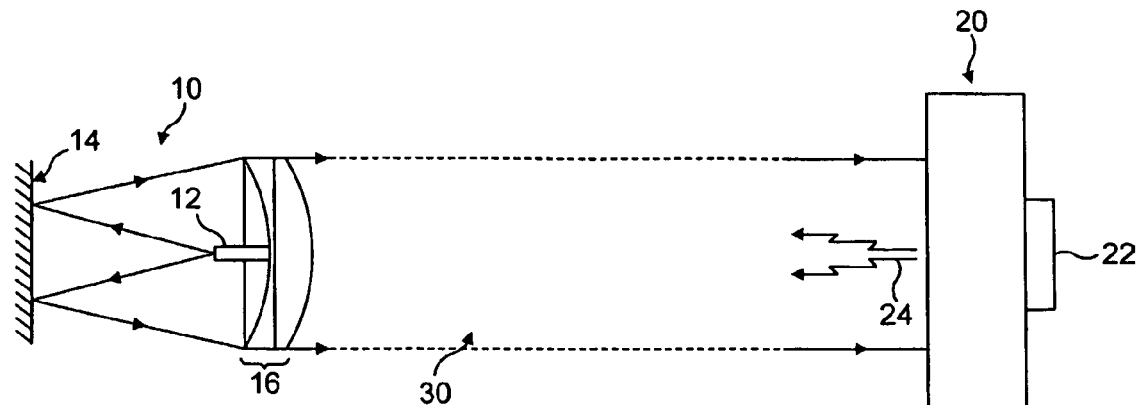
FIG. 3 is a schematic view of an open path gas detector according to the present invention showing both the transmitter unit and the detector unit.

FIG. 3 is a schematic representation of an open path gas detector according to the present invention, which includes a transmitter unit 10 and a detector unit 20. The transmitter unit transmits a parallel beam of radiation, which is generally denoted by the reference number 30, along a measuring path that can be a substantial length, for example 20 to 1,000 m.

The transmitter unit 10 includes a tuneable laser diode 12 that produces a beam of infrared radiation in a very narrow wavelength band that is directed rearwardly at a steerable mirror 14, that reflects the radiation towards an arrangement of optics 16 that collimates the beam reflected by the mirror to form the parallel beam 30 directed along the measurement path at the detector unit 20. The detector unit 20 includes filters (not shown) for filtering out radiation in wavelengths that are not of interest. After passing through the filters, the radiation is incident on a detector 22 that produces a signal that gives a measure of the intensity of the radiation incident on it. This signal is processed to extract the magnitude of the frequency components carrying information. These magnitudes are passed to a transmitter (not shown) that transmits a communication signal (shown schematically by arrows 24) back to the transmitter unit. The transmitter unit includes a receiver (not shown but described in detail below) that receives the transmitted signal 24.

The control and operation of the tuneable laser diode in the context of open path gas detection, including the tuning and scanning of the emitted wavelengths, are known, e.g. as described above in connection with the prior art; a novel gas detection regime is also described below.

The width of the wavelength band emitted by the laser 12 is narrower than the gas absorption band of a target gas. As in the system described in GB-2353591, the output wavelength of the laser is varied to scan across the gas absorption band of a target gas and this is achieved by varying, e.g. sinusoidally, the electrical current passed through the laser, which also varies the optical output power of the laser also sinusoidally. The variation in wavelength and power is brought about by driving the laser with a drive signal.

Figure 4A:
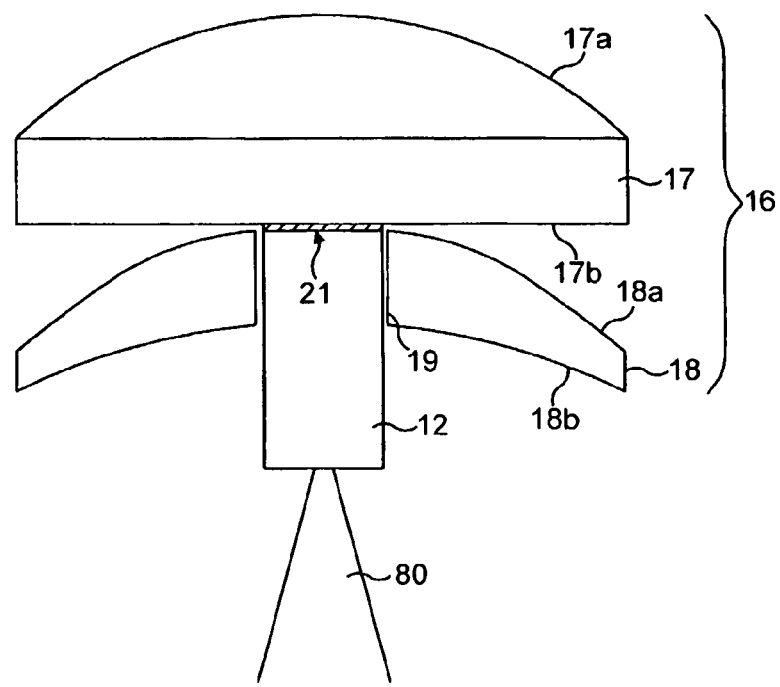
FIG. 4a is a cross section through the optic 16 of FIG. 4.

The system is shown in greater detail in connection with FIGS. 4 to 9, 15 and 16. Referring initially to FIGS. 4, 4a and 5, there is shown the optics 16, which is formed from a collimating lens 17, which forms the window from which the beam 30 is transmitted into the open path, and a correction lens 18, which is held in an adjustable mount (not shown in FIG. 4 but visible in FIG. 16). The front surface 17a of the collimating lens 17 is spherical and the rear surface 17b is flat while the front and rear surfaces 18a and 18b of the correction lens 18 are spherical. The laser 12 extends through an axial bore 19 in the correction lens 18 (see FIG. 4a). Electrical connections to the laser are provided in flexible connection 27, which is visible in FIG. 4.

The laser 12 may consist of the actual laser device, a temperature stabilising device such as a Peltier Effect heater/cooler, a temperature sensing device, a package window and possibly other components all mounted in a common housing.

Referring to FIG. 4a, the laser 12 is supported by a thermally conductive support element (not shown) and is adhered at one end to the flat rear surface 17b of the collimating lens 17 by a thin layer of adhesive 21, for example epoxy resin. Radiation is transmitted in a beam 80 rearwardly by the laser 12, i.e. in a direction away from the optics 16. In use, the tuneable laser diode 12 generates substantial heat and its temperature must be controlled within a narrow range and this is brought about by a thermoelectric cooling element (not shown) of known design that removes excess heat. However, additional cooling is provided by heat transfer to the collimating lens 17 across the adhesive bond 21 so that the collimating lens 17 in particular acts as a heat sink. The transfer of heat from the tuneable laser diode 12 to collimating lens 17 not only assists in the removal of energy from the laser 12 but also has the advantage of heating the lens 17.

In normal operation, it is necessary to heat the window of the transmitter unit, i.e. collimating lens 17, to prevent water condensing on it, which would otherwise obscure the radiation beam. Generally, the energy supplied by the transfer of heat from the laser to the collimating lens 17 will be insufficient to maintain the component at the desired temperature above the dew point. Accordingly, an auxiliary resistive heater (not shown, but of known design) is provided under thermostatic control to provide top-up heat to the collimating lens 17 to maintain it at the desired temperature. Thus the thermal bonding of the laser to the lens 17 reduces the amount of cooling that the laser 12 needs and also reduces the amount of energy required to heat the collimating lens 17. Heat from the collimating lens 17 is dissipated to the atmosphere.

Figure 15:
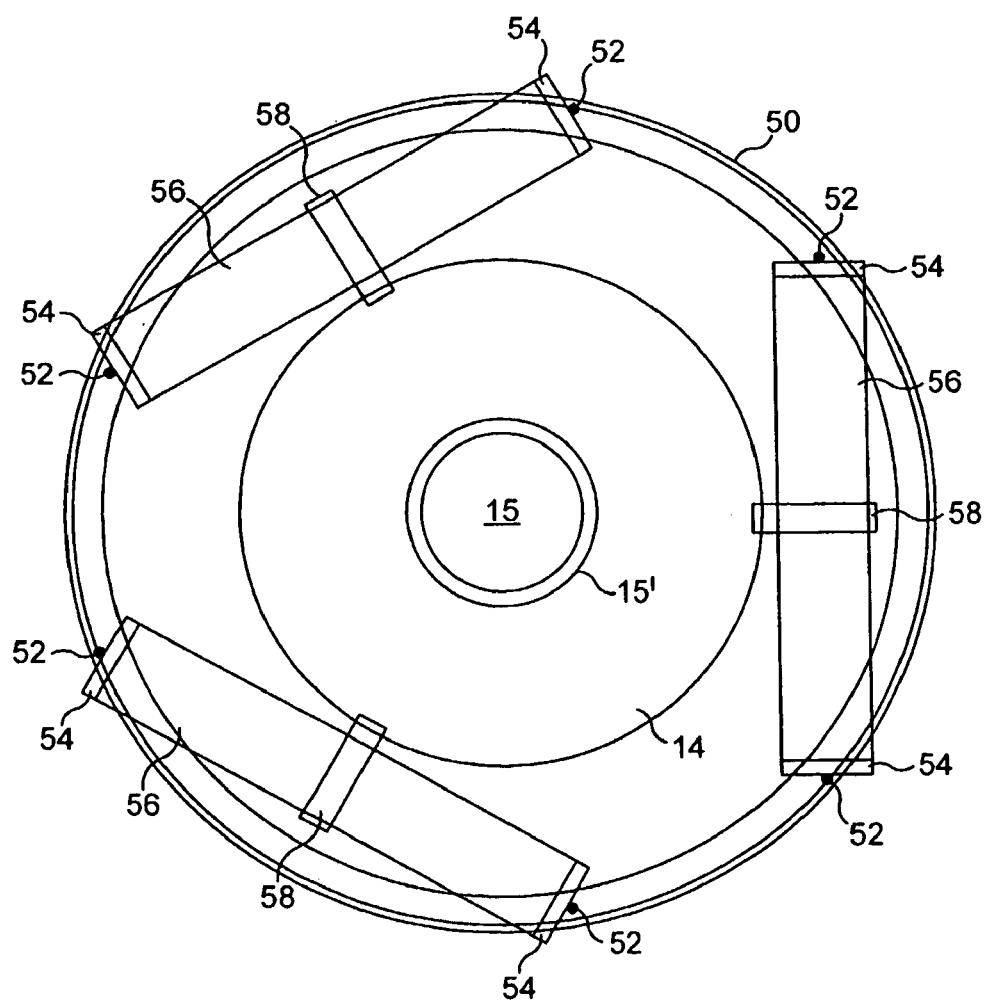
FIG. 15 is a plan view of the mirror arrangement of the transmitter unit of the open path gas detector of FIGS. 4 and 5.

The transmitter unit 10 includes a mounting ring 50 (see FIGS. 4, 5 and 15) having three pins 52 that hold end pieces 54 each of which has a socket for clamping the ends of a piezoelectric strip 56. Three such piezoelectric strips are provided, as shown in FIG. 15. FIG. 15 differs from the arrangement in FIGS. 4 and 5 in that the FIG. 15 arrangement provides six mounting pins 52, two for each piezoelectric strip, whereas in FIGS. 4 and 5 only three mounting pins 52 are provided, i.e. each mounting pin holds the ends of two piezoelectric strips. The piezoelectric strips are model numbers PL 127.10, which are commercially available from PI Ceramic of Lederhose, Germany (www.pi.ws).

The strips 56 are held firmly at each end by the end pieces 54 and the application of electrical potential to the strips causes them to flex; such flexing can take place in a time less than 2 milliseconds. Depending on the potential applied, the centre of the strip can be moved reliably by distances of up to 0.25 mm.

Halfway along their length, each of the three strips 56 is provided with a collar 58. One end of the collar 58 is clipped over the rim of the steerable planar mirror 14. The mirror is annular in shape and has a central opening 15. The opening may be a physical hole or a non-reflecting area, which is preferably transparent or translucent. There is a non-reflective area 15' around the opening 15 to increase the area of the central part of the mirror that does not reflect the incident radiation, as explained in further detail below. The three clips 58 support the mirror and allow it to be moved by the piezoelectric strips 56 when they are flexed. A suitable control algorithm co-ordinates the movement of the individual strips, making it possible to steer the mirror in a desired direction, thereby also changing the direction of the beam 30 provided along the measuring path. Using the strips, it is possible to sweep the beam in a predetermined manner, e.g. in a circular or elliptical path, as discussed below.

Instead of clamping the ends of the strips 56 using a number of mounting pins 52, as described, a single frame may be provided for holding the strips; such a frame could be rigid and so help reduce cross-vibrations being transmitted from one strip to another.

The strips will resonate at a frequency of above 500 Hz and so it is possible to cause the strips to move without resonance at frequencies of up to about 500 Hz. The manufacturers of the strips only specify a use of the strips that are operated in cantilever fashion in which they are anchored at one end only. We have found that, by anchoring them at both ends, the resonant frequency is substantially increased, which greatly increases the speed of response of the system of the present invention.

Instead of providing three strips 56, two strips and an anchoring point can be provided since such an arrangement will also be able to steer the mirror.

Because the mirror 14 can be steered accurately and quickly by the strips, it is possible to bring about alignment in a time of the order of 0.005 to 0.01 sec and so it is possible to maintain alignment even though the detector unit is moving/vibrating with a frequency of the order of hundreds of Hz. In addition, the strips can provide adjustment of the position of the mirror 12 in the axial direction (z-direction) if required.

Figure 6:
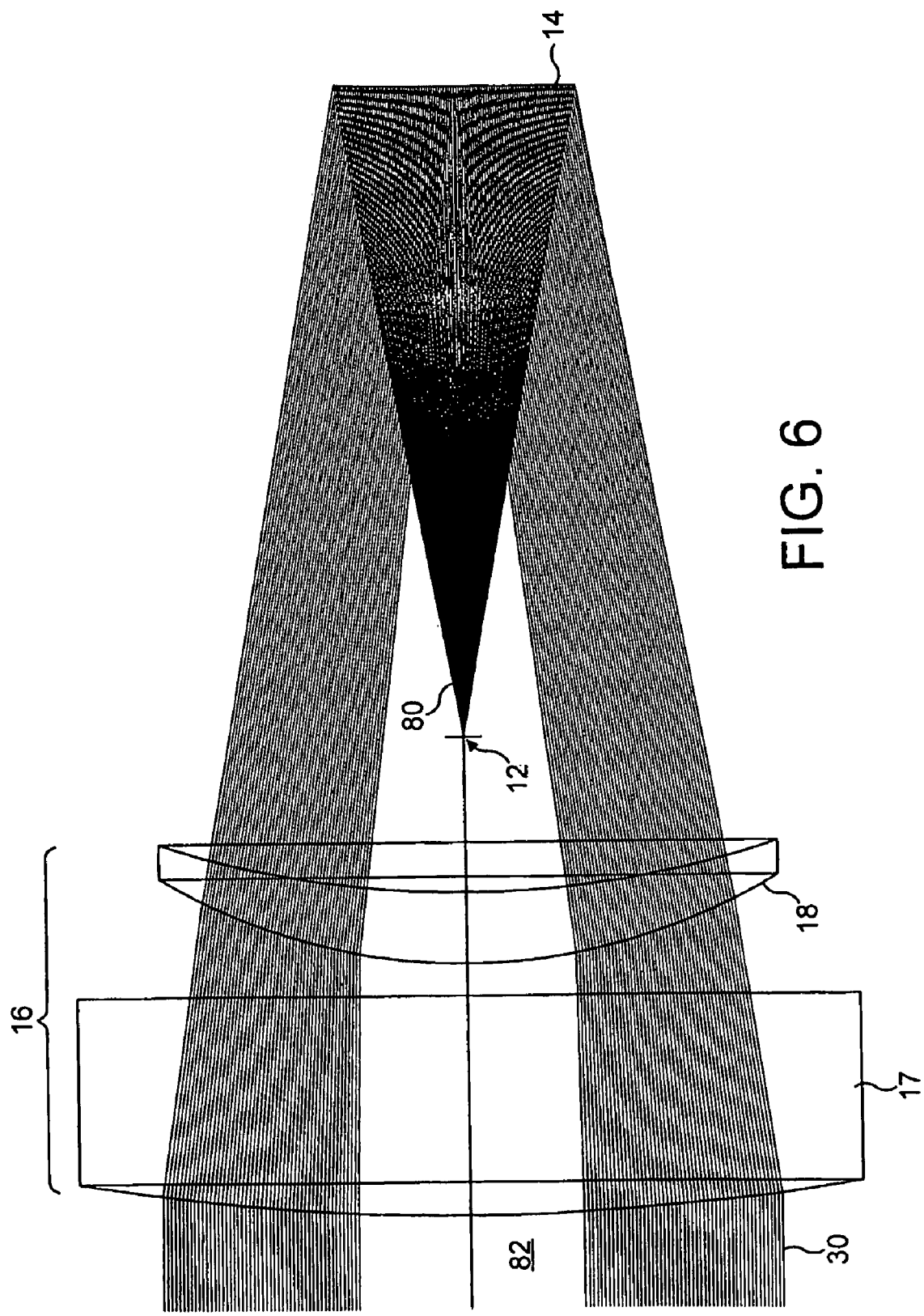
FIG. 6 is a ray diagram showing the transmission of the beam along the measuring path.

FIG. 6 shows the arrangement for producing the main beam 30 along the measurement path. The tuneable laser diode 12 directs a beam 80 at the mirror 14, which reflects the beam towards the optics 16, which forms the parallel beam 30 along the measurement path. The beam 30 has a central shadow 82 formed because the central part of the beam 80 either passes through the central hole 15 in the mirror 14 or is absorbed by the non-reflective area 15', rather than being reflected back by mirror 14. The laser diode 12 is located in this shadow.

As is evident from FIG. 6, a small movement of the mirror can alter the direction of the beam 30 or, in other words, the mirror 14 steers the beam 30.

The optimum diameter of the shadow 82 in the beam and the optimum diameter of the beam passing through the opening are independent of each other and it may well happen that it is desired to make the diameter of the shadow 82 in the beam 30 larger than would be provided simply by the opening 15. In this case, the diameter of the non-reflective area 15' is set to provide the required diameter of the shadow 82.

It is not necessary to place the laser on the axis of the mirror, as shown in FIG. 6, and instead the laser can be placed off-axis but in that case it would be difficult to arrange the laser so that the heat it generates can be used to heat the collimating lens 17.

Figure 7:
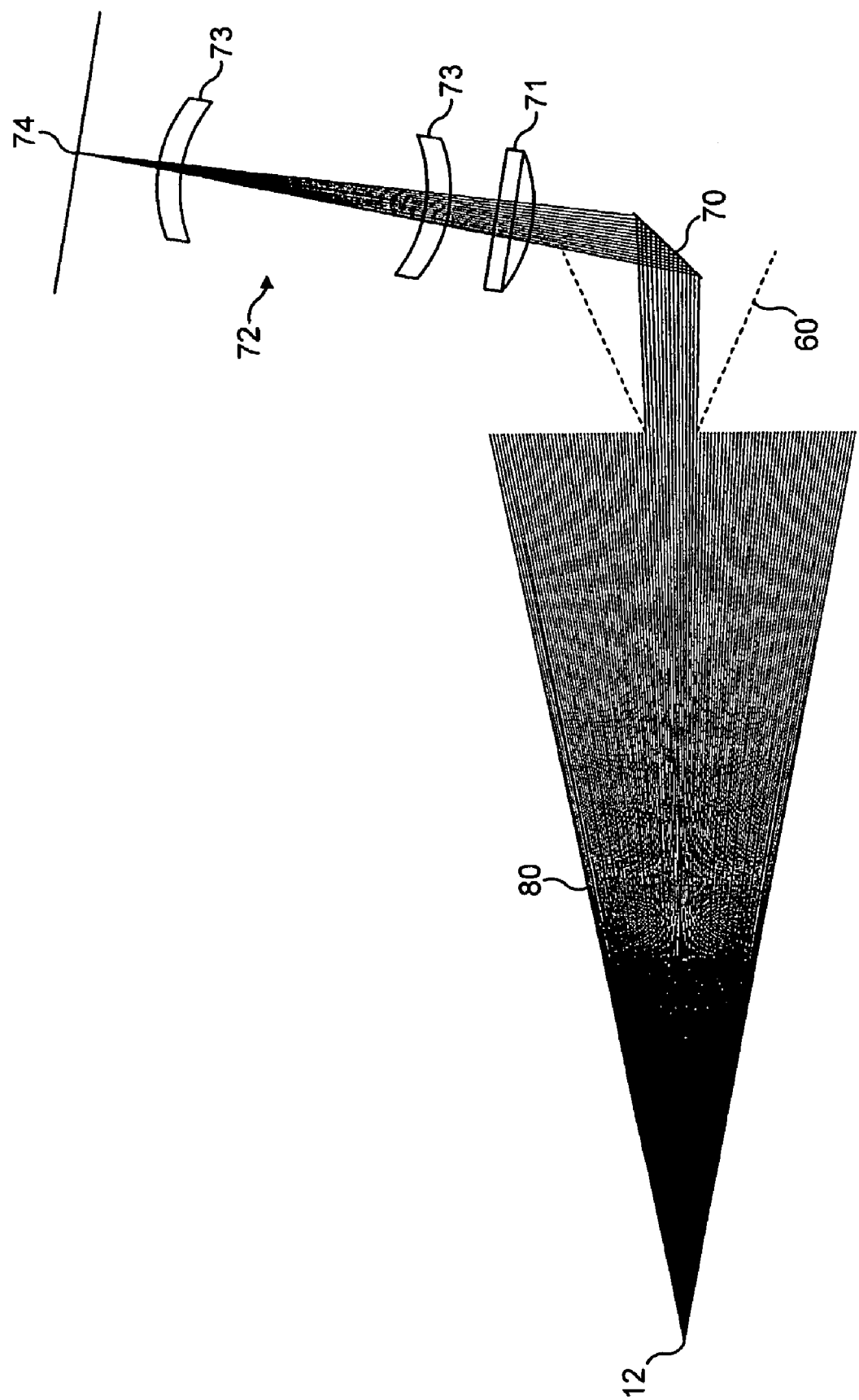
FIG. 7 is a ray diagram showing the provision of a wavelength locking beam in the detector unit of the present invention.

Referring to FIGS. 4 and 5, a truncated conical radiation-absorbing body or shield 60 is provided behind the mirror 15. The body 60 has a hole of 1.5 mm diameter in its truncated surface 62. The body 60 is hollow and a lens 66 is provided at its base. Centrally mounted on the lens 66 is a support 68 having a mirrored surface 70 that is angled with respect to the axis of the detector unit. The angled surface 70 reflects radiation entering the body 60 through the truncated surface 62 and directs it towards a sample cell 72, which holds a sample of the target gas. This arrangement is shown in the ray diagram of FIG. 7 where the beam produced by the laser 12 is shown at 80. Most of the beam strikes the mirror 14 and is reflected towards the optics 16, although the reflected beam is not shown for the sake of clarity. However, part of the beam passes through the hole 15 in the centre of the mirror and then passes through the hole in the truncated surface 62 of the body 60, where it is incident on the angled mirror 70 and is reflected via collimating lens 71 through the gas sample cell 72. The walls of the gas cell 72 are shown in FIG. 7 by the reference number 73 and act as lenses that, together with the lens 71, focus the radiation passing through the cell 72 onto a radiation detector 74.

The use of a reference gas cell and detector is well-known in open path gas detection using a tuneable laser diode and its use is outlined above in connection with GB 2353591. The reference gas cell mimics the situation of the main beam 30 along measuring path when target gas is present. By providing target gas within the cell 72, the wavelength of the radiation from the laser can be ascertained relative to the fixed absorption band of the target gas, and the laser can be adjusted if necessary, so that the wavelength of the radiation emitted by the laser can be maintained at the correct wavelength.

Referring back to FIGS. 4 and 5, the diameter of the surface 70 reflecting the gas reference beam is the same as or just greater than the diameter of the beam passing through the hole 62 in the radiation absorbing surface 60 so that none of the beam 80 strikes the lens 66 on which the support 68 and the reflecting surface 70 are mounted.

Figure 8:
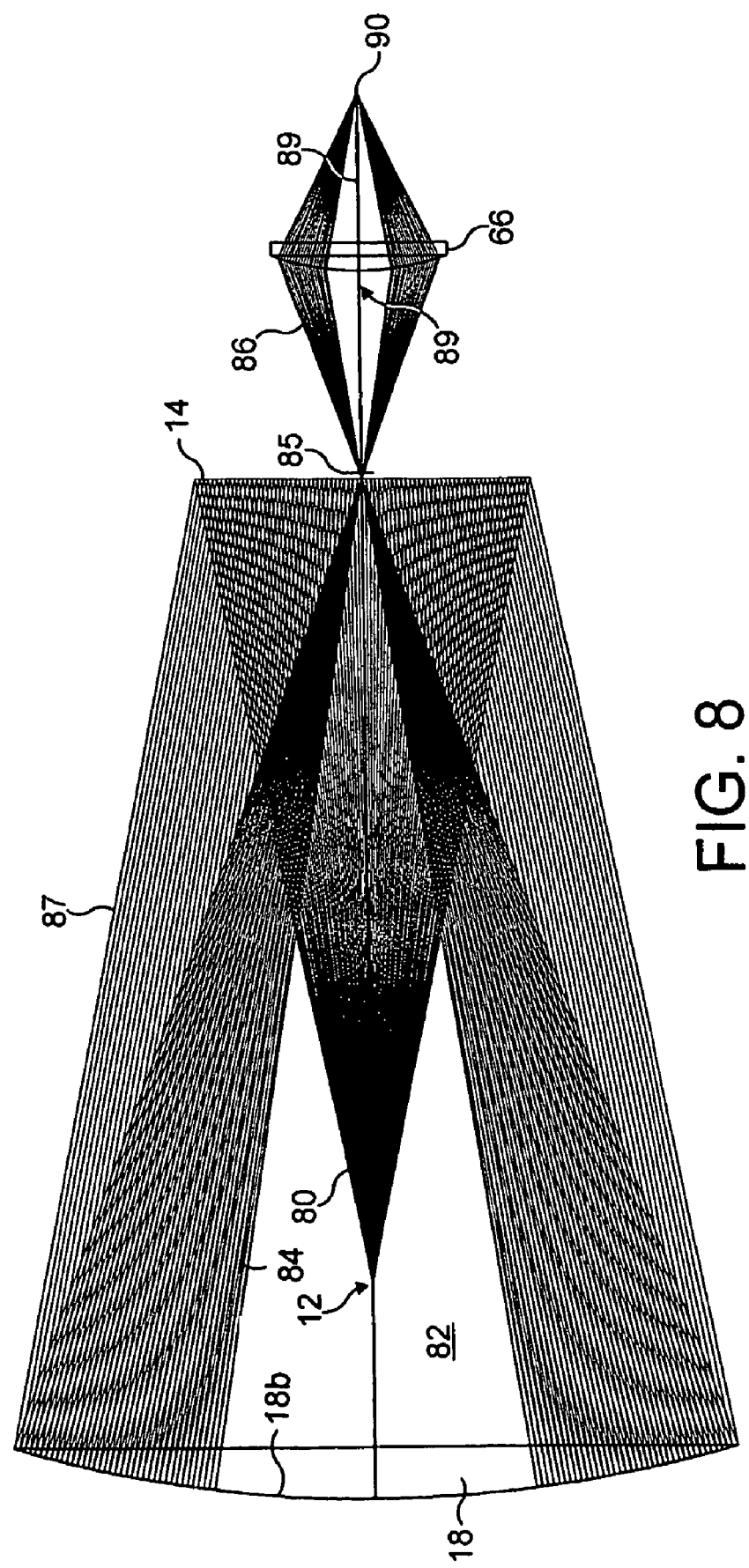
FIG. 8 is a ray diagram showing the provision of a reference beam in the transmitter unit.
Figure 9:
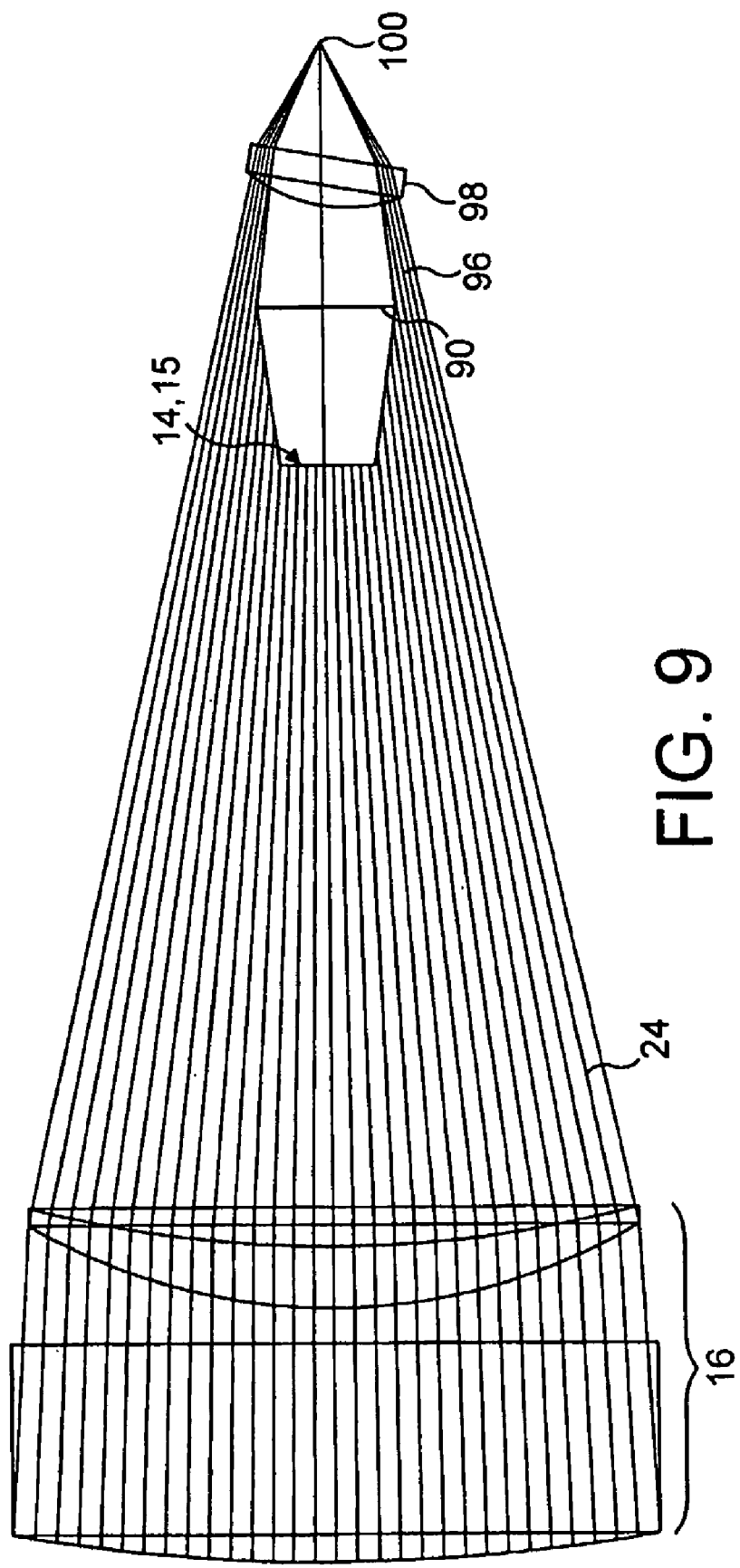
FIG. 9 is a ray diagram showing the communications link between the detector unit and the transmitter unit.

Turning now to FIG. 8, the beam 80 produced by the tuneable laser diode 12 is shown being reflected by the annular mirror 14 to produce a beam 87 directed at the optics 16. The beam 87 passes through the optics arrangement 16 to form the parallel beam 30 (see FIG. 6). However, a small fraction is reflected from the back surface 18b of the correction lens 18. The back surface 18b is spherical and has a curvature such that it reflects the beam 87 to form a beam 84 that has a focal point 85 at or near the hole 15 in the centre of the annular mirror 14. The back surface need not be spherical and other optical forms can be used so long as it converges the radiation so that it passes through the hole 15 in the mirror 14, which is preferably as small as possible so as to minimise radiation passing from behind the mirror 14, through the hole and towards the laser 12, where it could cause interference fringes. A beam 86 of radiation therefore passes through the hole 15 of the mirror 14 and the hole in the truncated surface 62 of the conical body 60 and is incident on the collimating lens 66 that supports the oblique reflecting surface 70. The lens 66 focuses the beam 86 on to a reference detector 90. The reference detector 90 provides a measure of the radiation actually emitted by the laser 12 and is used in the processing of the signal recorded by the detector unit 20, as described below. It is important to note that the above arrangement passes radiation from the whole of the cross section of the radiation beam that is transmitted to the detector unit 20 and so the reference beam is truly a measure of the transmitted radiation, rather than a sample of part of the beam.

It will be seen in FIG. 8 that the hole 15 in the middle of the mirror 14 casts a shadow 82 in the middle of the beam 87, which in turn forms a shadow 89 in the centre of the beam 86. This shadow encompasses the oblique reflecting surface 70 and accordingly none of the beam 86 falls on, and hence is reflected by, the surface 70 towards the gas reference cell 72.

Referring back to FIG. 3, the data concerning the radiation detected by the detector unit 20 is transmitted back (as shown schematically by the reference number 24) to the transmitter unit 10, where it is incident on the optics 16 which (see FIG. 9) focuses the communication signal towards the mirror 14. However, the mirror is such that it is transparent at the wavelength of the communication signal and accordingly beam 24 passes through the mirror. It is alternatively also possible to discriminate the communications signal from the radiation forming the beam 30 on the basis of the wavelength of the communication beam, e.g. by causing it to impinge on a diffracting medium, which will cause the communication radiation beam 24 to be diverted at a different angle as compared to the beam 80; the communications detector can then be placed in a position to receive the diverted beam 24.

The outside of the truncated conical body or shield 60 blocks the radiation incident upon it since it is absorbed by the conical body or is reflected by the outer wall of the conical body 60 in a direction away from the detectors 74,90,100 in the transmitting unit 10 and accordingly does not interfere with the operation of the detectors. The only exception is the radiation that passes through the hole in the truncated surface 62 and is incident on the reflecting surface 70, which reflects the communication radiation towards the gas cell 72. However, the communication radiation does not affect the operation of the wavelength locking control but even if it did, the communications radiation could be filtered out of the radiation passing to the gas cell 72 by applying a coating to lens 71 that absorbs or reflects radiation at the wavelength of the communication beam. Any communications radiation falling on the lens 66 will be focussed onto, and be blocked by, the detector 90 for the reference beam but has a minimal effect on the reference detector 90.

The communications radiation 24 that passes around the outside of the truncated conical body 60, is in the form of annular beam 96 which is incident on a collimating lens 98 (see also FIG. 5) where it is focused on a communications detector 100 which produces a signal containing the data form the communications radiation 24; the signal is fed into a microprocessor (not shown). The reference detector 90 is mounted on the communications lens 98 but does not interfere with the communications signal since the part of the lens supporting the reference detector is in the shadow cast by the body 60 on the communications beam.

It will be noticed in connection with FIGS. 4 and 5 that the communications lens 98 is not orthogonal to the optical axis of the detector unit 10 but rather is slanted with respect to this axis; this is in order to avoid radiation being reflected by the lens 98 or the detector 90 back towards the laser diode 12, which would cause undesirable interference fringes. For the same reason, any component in the transmitter unit 10 that could reflect radiation to combine with the laser radiation transmitted to the receiver unit 20 is preferably slanted with respect to the axis.

Figure 16:
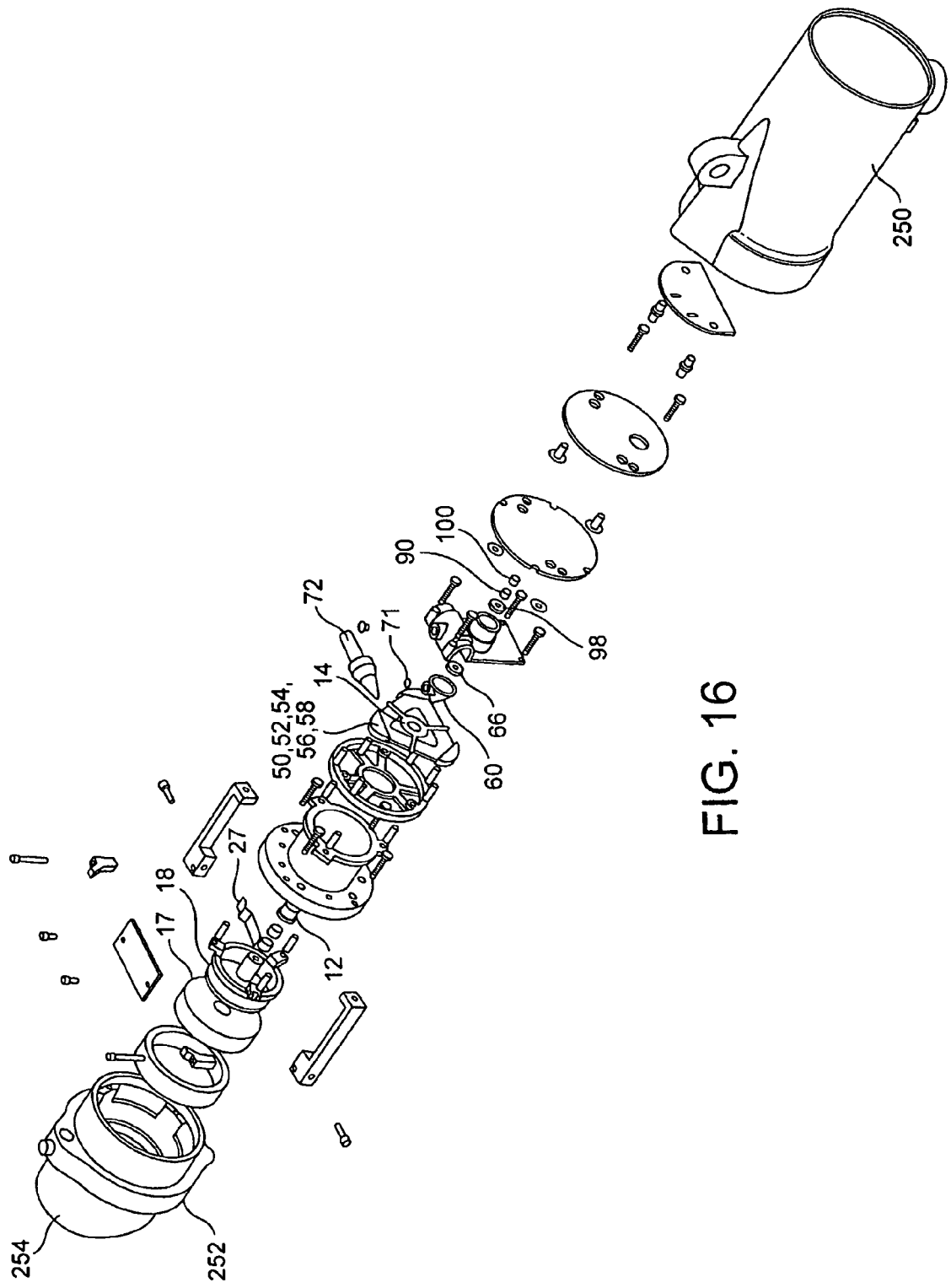
FIG. 16 is an exploded view of a transmitter unit according to the present invention.

FIG. 16 is an exploded view of the transmitting unit 10 described above showing the assembly of the components in a housing 250 in a highly compact manner. The housing is closed by an end cap 252 provided with a sun shield 254.

A microprocessor controls the operation of the transmitter unit 10 and analyses the signal 24, as received by communications detector 100, together with the signals from the wavelength tracking detector 74 and the reference detector 90 to produce an analysis of the target gas in the measurement path. The processing of the various data and the principles underlying that processing are outlined below.

The reference data derived from the detector 90 is used to compensate for perturbations arising from the laser/electronics and some fringe processes by performing an analysis on the output of the reference detector that is similar to the analysis applied to the output of the main detector 22 in the receiver 20. The result of the analysis of the output of the reference detector 90 then provides a baseline against which the output of the main detector 22 in the receiver can be compared, thereby eliminating the perturbations from the gas signal analysis.

It should be noted that the arrangement described above does not include a beam splitter to provide the reference signal or the wavelength tracking signal, which is highly advantageous since beam splitters produce interference fringes with coherent radiation. If interference fringes are present, the change in intensity between the bright and the dark parts of the fringes can be greater than the signal attenuation resulting from the presence of target gas in the measurement path, making it unreliable in the detection of the target gas. Accordingly, the avoidance of such interference fringes is highly advantageous.

It is important that the detector unit 20 is accurately aligned with the transmitter unit 10. The transmitter unit 10 produces a relatively narrow beam 30 with a divergence of preferably less than 0.1° in order to maximise the intensity of the radiation reaching the detector 22. On the other hand, the detector 22 has a wide reception range, i.e. it will detect radiation incident on it from a relatively wide arc, e.g. about 1°. Because the beam 30 is narrow, if it is not properly aligned with the detector 22, the intensity of the radiation reaching the detector falls away sharply and it is then much harder to detect the attenuation of the beam caused by target gas in the measurement path. However, the alignment between the transmitter and detector units 10, 20 can change relatively rapidly; for example, the transmitter and detector units could be located on an offshore oil platform and the twisting of the structure of the oil platform in high winds and rough seas can result in misalignment. This misalignment may vary since the detector unit will sway with respect to the transmitter unit 10 at a frequency dictated by the structure of the oil platform. The movement of the detector unit and/or the transmitter unit can have a frequency of several Hz up to several hundred Hz and the present invention can track such movement and align the transmitted beam to the detector unit to compensate for the movement, as discussed below.

Likewise, if the detector unit and/or the transmitter unit is mounted on a post in permafrost in the Arctic oil fields, the permafrost can melt during the daytime causing the position of the post to shift and resulting in misalignment between the transmitter unit 10 and the detector unit 20. The misalignment can increase over the space of a few hours and again the present invention can track such movement and align the transmitter and detector units, as will now be described.

Figure 10:
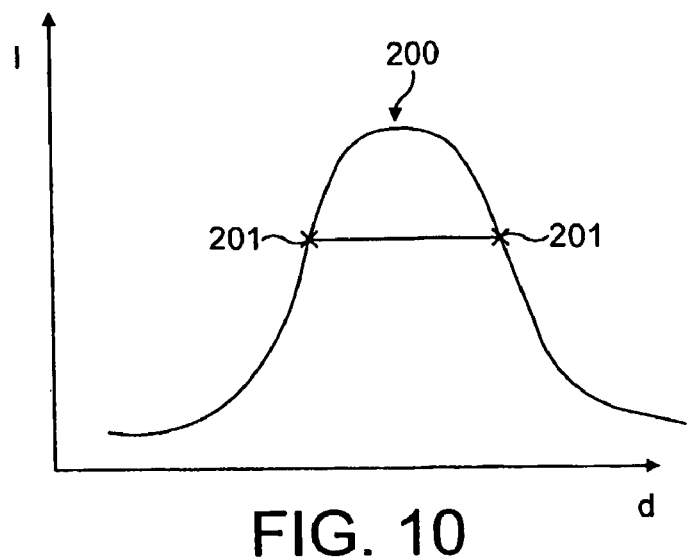
FIG. 10 is a graph showing the variation of the intensity of the radiation detected against the angular distance between the optimum beam and the actual beam.

Referring to FIG. 10, there is shown the drop-off in intensity in the beam measured by the detector unit 20 as a function of the angular distance of the detector unit from exact alignment with the beam 30 (the signal at exact alignment is shown by point 200). As can be seen, if the alignment differs from the optimum position at 200, the measurement signal falls rapidly.

Figure 11:
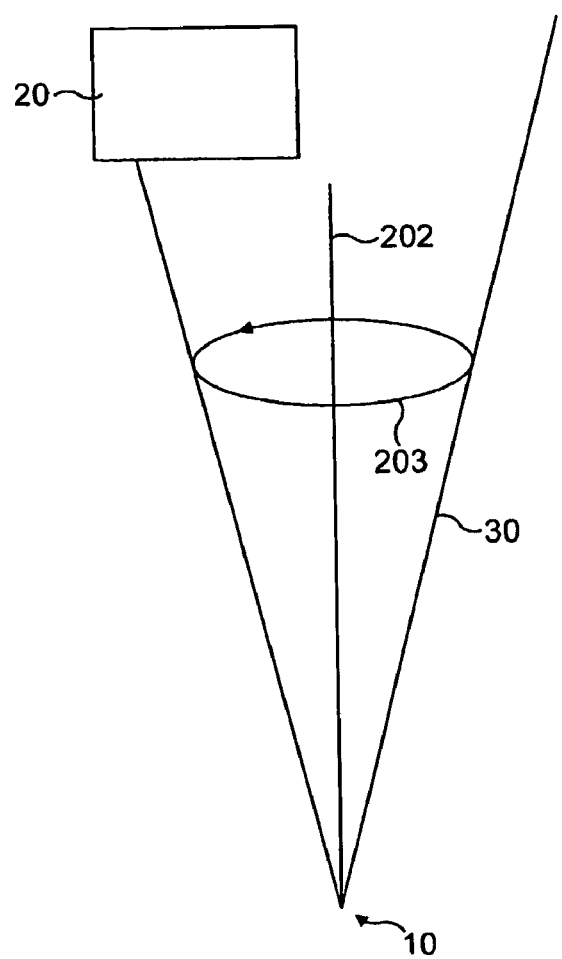
FIG. 11 is a schematic view showing the scanning of a radiation beam from the transmitter unit.

Referring to FIG. 11, the optimum alignment is found by moving the beam 30 in a circular path 203; this is achieved by steering the mirror 14 using the piezoelectric strips 56. Since the strips can be moved at a frequency of the order of hundreds of Hz, the beam can be directed around the circular path rapidly. If the detector unit is aligned along the central axis 202 of the rotated beam, the intensity of the beam at frequency 1f (i.e. the frequency at which the beam is moved around the path 203) will not change with time since the detector will remain equidistant throughout the path 203, see points 201 in FIG. 10. However, if the detector is located off the central axis 202, the signal will vary as the beam moves around its circular path 203. This is illustrated in connection with FIGS. 12 and 13.

Figure 12:
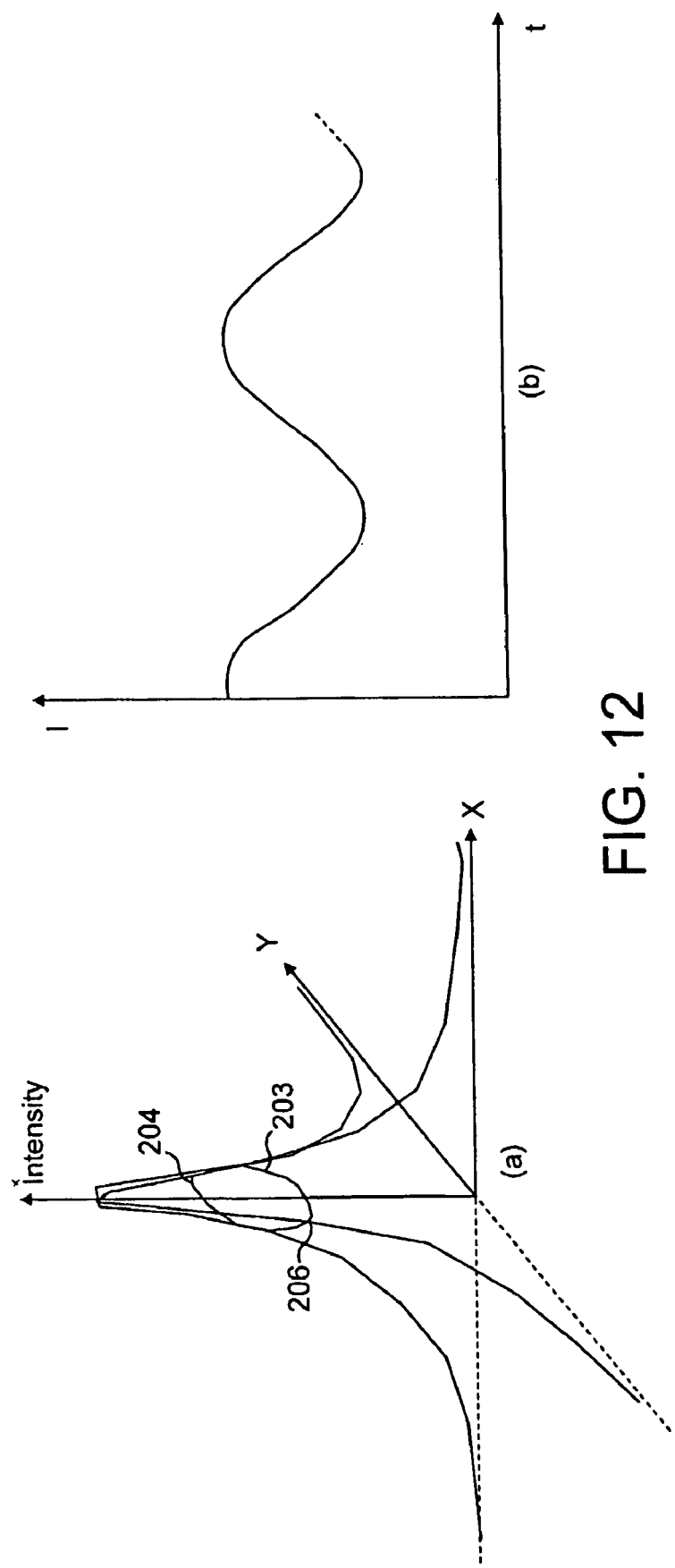
FIG. 12 is a variant of FIG. 10 showing the effect of a scanning radiation beam on the intensity of radiation detected by the detector unit.

FIG. 12(*a*) is a 3-dimensional plot showing the drop off in the signal of the detector 20 as a function of the angular distance of the detector unit from exact alignment with the beam 30. The signal when there is exact alignment is the signal on the z axis of the plot of FIG. 12(*a*). If the circular path 203 of the beam is not centred on the z axis, the beam in one part 204 of the circular path will be closer to alignment than the diametrically opposite part 206. Thus, at position 204, when the beam is closest to alignment with the detector, the signal will be at a maximum and when it is most out of alignment, at position 206, the signal will be at a minimum. The detector 22 therefore registers radiation that fluctuates sinusoidally, as shown in FIG. 12*b*.

The phase of the signal can be detected using a phase-sensitive measuring amplifier (lock-in amplifier) that collects the signal from the detector 22. Fourier transform analysis can provide details of the phase of various components of the signal.

In FIG. 12(*a*) the detector 22 is located along the −Y axis relative to the z axis, i.e. the beam 30. Therefore, the signal recorded by the detector, which is shown in FIG. 12*b*, is a cosine wave having a frequency equal to the frequency of the beam along path 203. For a given circular path, the amplitude of the signal will indicate the distance from exact alignment. Thus it is possible to obtain a measure of the magnitude of the misalignment from the amplitude of the signal at the frequency at which the beam is moved around path 203.

Figure 13:
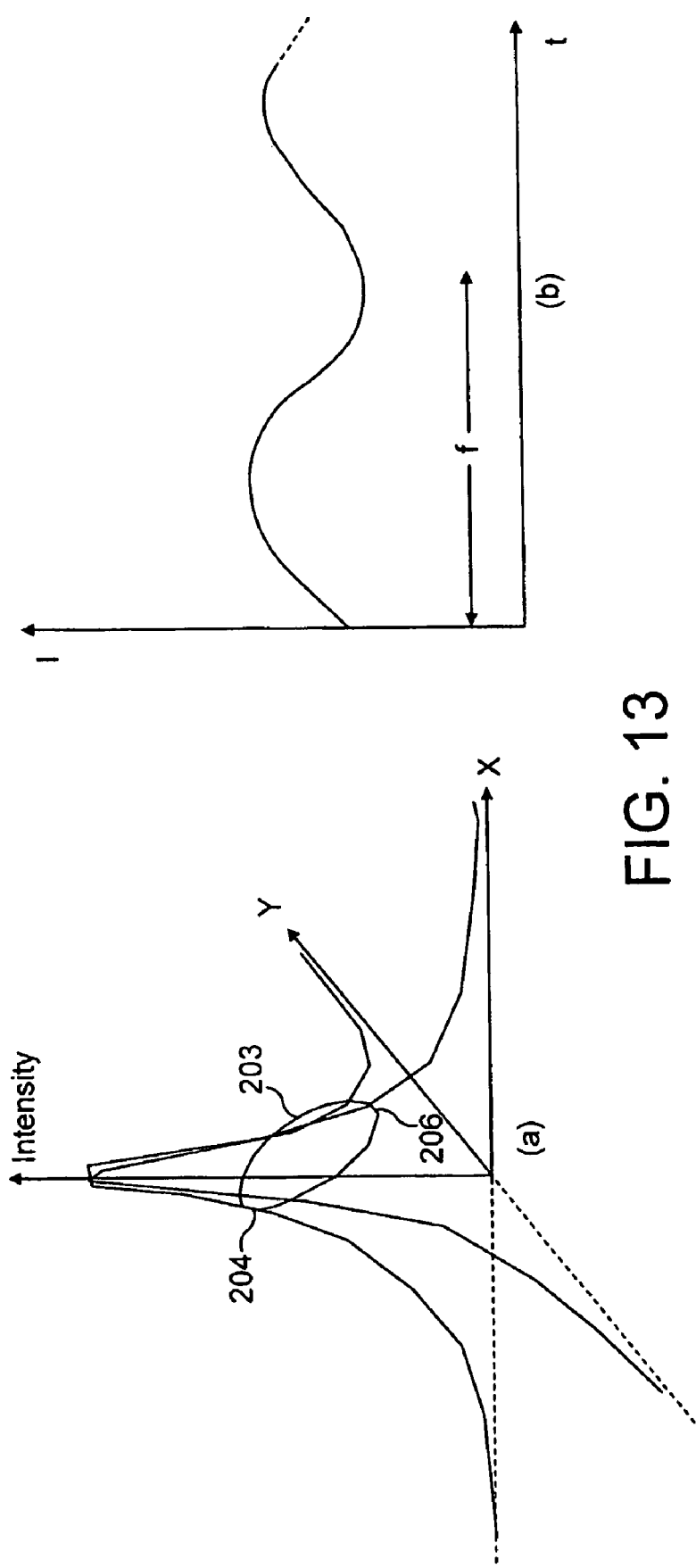
FIG. 13 is similar to FIG. 12 except it shows a different variation of alignment.

From the phase of the signal at the frequency at which the beam is moved around path 203, it is possible to detect the direction of misalignment. This is illustrated in connection with FIG. 13, which is identical to FIG. 12 except that the detector unit 20 is located along the +X axis relative to the z axis, i.e. the beam 30. In the case of FIG. 13, the phase of the signal is shifted by 90° (see FIG. 13(*b*)) as compared to that of FIG. 12(*b*), i.e. it is a sine wave rather than a cosine wave. Thus by measuring the phase of the signal at the frequency that the beam is moved around the path 203 using Fourier transform analysis of the signal, it is possible to discern the direction of misalignment of the beam 30, according to the following table:

| Direction of misalignment | Phase of the signal using Fourier transform analysis |
| --- | --- |
| +X | +cos |
| +Y | +sin |
| −X | −cos |
| −Y | −sin |

Most misalignments will not fall exactly on one or other of the X and Y axes and in that case the signal will provide a component from each of the two axes that the misalignment lies between. For example if the beam is aligned on a point falling between the +X and −Y axes, the Fourier transform of the signal will have a component of +cos and a component of −sin. The relative magnitude of these two phase components will indicate the angular position between the +X axis and the −Y axis.

Accordingly, it is possible to find the direction and magnitude of the misalignment from the amplitude and phase of the signal 24 at the frequency of rotation of the beam, and it is therefore possible to know the direction that the beam needs to be moved to bring it into alignment. As the alignment approaches optimum, so the amplitude of the signal 24 (as shown in FIGS. 12*b* and 13*b*) decreases. At optimum alignment, no variation at frequency 1f (the frequency at which the beam 30 is moved around the path 203) should be observed if the path around the detector is circular, see FIG. 10.

The initial alignment of the beam can be brought about using a relatively large-diameter path 203 so that the detector unit 20 falls within the path and then the diameter of the path can be narrowed as the central region of the looped beam path approaches alignment with the detector 22; at optimum alignment, a gas reading may be taken.

Instead of moving the beam in a circular path, it is possible to move it in an elliptical path, in which case a variation of the signal 24 will take place at a frequency of twice the frequency f of the beam around the path. In addition higher even harmonics, 4f, 6f etc will be generated. An advantage of using an elliptical path rather than a circular path is that it generates a 2f signal and higher harmonics, even when approaching optimum alignment of the beam 30 and the detector unit 20. The ratios of the various harmonics give information on the magnitude of the misalignment and also allow a means for assessing the optimum diameter of the elliptical path 203. With a non-circular, e.g. elliptical, path, the signal at frequency 1f is reduced to zero when the detector is centrally located within the loop, however signals at some higher harmonics such as 2f and 4f will still be present.

Figure 14:
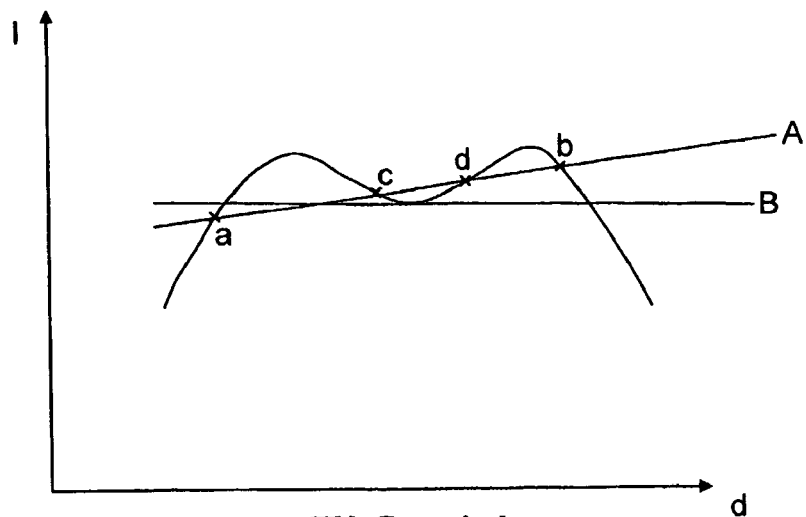
FIG. 14 is a more detailed view of the peak of the graphs of FIGS. 10, 12 and 13.

Referring back to FIG. 6, it can be seen that there is a shadow 82 in the transmitted beam 30. This manifests itself as a "dimple" at the peak of the signal as shown in FIG. 14. It is therefore possible to find the optimum alignment using the above technique with an elliptical path 203. When the beam 30 is narrowed to the area of the dimple, the frequency of the signal showing any misalignment will increase to twice the frequency that occurs with a larger diameter (that is at a frequency of 4f). This can be seen from line A in FIG. 14 where the major axis of the elliptical path form maximum and minimum at points b and a and the minor axis of the elliptical path form maxima and minima at points d and c respectively. The presence of a 4f signal can be used to detect an approach to alignment. As before, at optimum alignment, there is no variation in the signal at frequency 1f, as shown by line B.

Figure 17:
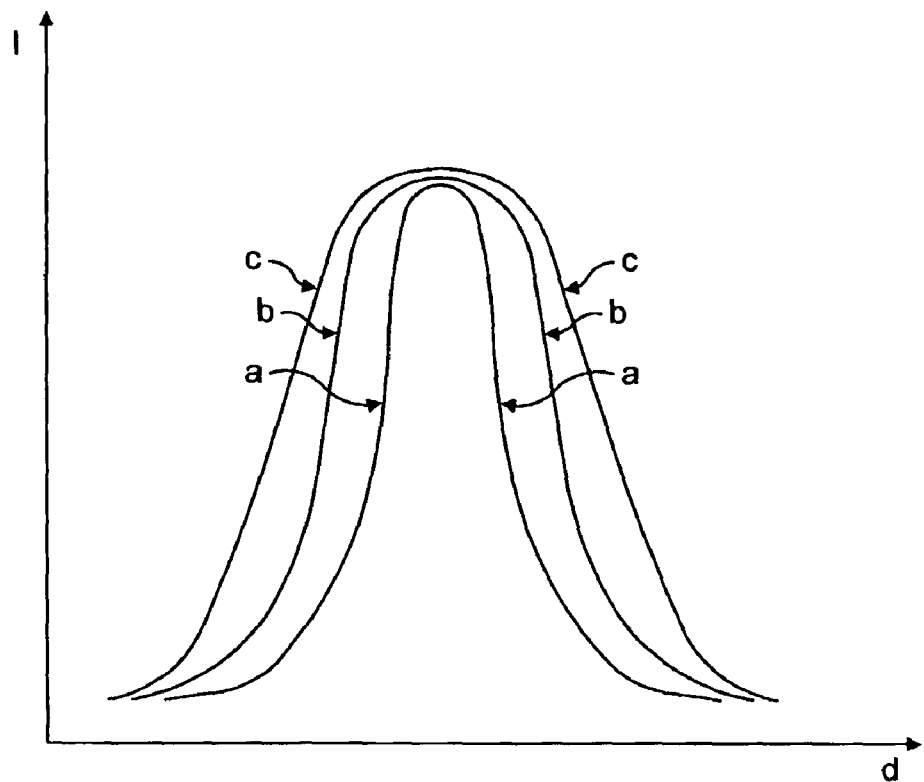
FIG. 17 is a graph showing the variation of the intensity of the radiation detected against the angular distance between the optimum beam and the actual beam at various path lengths.

The movement of the beam about a circular or elliptical path 203 can also be used to measure the distance between the detector and the transmitter units 10,20. The width of the curve of intensity against misalignment angular distance (see FIG. 17) decreases as the separation between the transmitter and detector units increases. For a given distance between the detector and the transmitter units, a curve can be plotted when the transmitter and receiver units 10, 20 are in alignment by starting with a wide diameter path 203 and gradually decreasing it. The full width half height (FWHH) of the curve of FIG. 17 is related to the distance between the detector and the transmitter units by an inverse relationship, and so the distance between the transmitter and detector units can be derived from the FWHH (or other measure of the width) of the curve. FIG. 17 shows three such plots a,b,c at three different distances between the detector and the transmitter units—curve a denoting the plot with the largest distance between the detector and the transmitter units and curve c being the plot with the smallest distance between the detector and the transmitter units.

The distance between the detector and transmitter units is important since, for a given average concentration of target gas between the two units 10, 20, the gas measurement signal will increase with increasing distance between the units. Therefore, the distance between the units is important to find the average concentration of target gas in the path between them. Generally, it is only necessary to establish the distance between the detector and the transmitter units once when they are first installed.

The alignment between the transmitter and detector units can be checked periodically to ensure it is optimum. However, it will often be the case that there is a forced vibration of either the transmitter unit or the detector unit or both. The vibration will induce variations in the measured signal in the same way as described above with respect to misalignment since vibration causes misalignment. By submitting the signal 24 to a Fourier transform, it is possible to find the frequency phase, magnitude and direction of the vibration in a similar way as described above in connection with aligning the beam 30 with the detector unit. Knowing the frequency phase, magnitude and direction of the vibration allows the mirror 14 to be steered to follow the path of the vibrations and so maintain alignment despite the vibrations. Obviously, the above measures will only be effective to eliminate the effects of misalignments caused by frequencies below the maximum frequency at which the mirror can be steered. The arrangement described above can steer the mirror at a frequency f of up to 500 Hz and so vibrations having a frequency of up to several hundred Hz, say 300 Hz can be accommodated in this way, which covers most of the vibrations that will be encountered in practice. The steerable mirror provides several advantages:

- It facilitates accurate alignment of the beam 30 and hence provides high coupling efficiency between the transmitter and the receiver units 10,20, thereby allowing the open path gas detector to tolerate high degrees of atmospheric attenuation e.g. by fog;
- It allows alignment errors due to relative movement between the transmitter and the receiver units 10,20, to be compensated for; such errors can arise for example from a change of position of the transmitter and/or the receiver units 10,20 or from vibration; even vibrations up to 150 Hz or even higher can be followed by the steerable beam;
- It allows the optics in the receiver unit to be of relatively small diameter, thereby reducing cost, since the beam 30 will be accurately aligned by the steerable mirror and therefore large diameter optics to capture the beam even when slightly out of alignment is not necessary; and
- The accurate alignment allows a narrowly divergent beam 30 to be used, e.g. with a beam divergence <0.25°, ideally <0.1°; a narrow beam divergence allows the intensity of radiation reaching the detector unit to be maximised.

The above describes the alignment of the beam with the detector. There will now be described a method of detecting target gas assuming that the detector is aligned with the beam 30.

Within the Background Art section, details were given of a basic technique that can be employed within a gas detector using a laser diode transmitter to measure the amount of a target gas within the path 30 between the transmitter 10 and the detector 20 involving calculating the 2f:1f quotient to provide a measure of the amount of the target gas in the path, where f is the frequency at which the laser diode is scanned across its wavelength range. Attention was drawn to the problem arising from harmonic distortion of the signal inherent within this technique, that is to say, harmonic distortion of the gas measuring signal at the modulation frequency f will also generate additional signals at a frequency of 2f (the gas measurement frequency) leading to inaccuracies of the gas measurement.

A solution to such problems is provided by the use of a laser modulation technique whereby the signal that results from the absorption of the optical signal by the gas is localised to frequencies that are not harmonics of the modulation frequency or frequencies of the signals, i.e. 1f, 2f, 4f etc.

Figure 18:
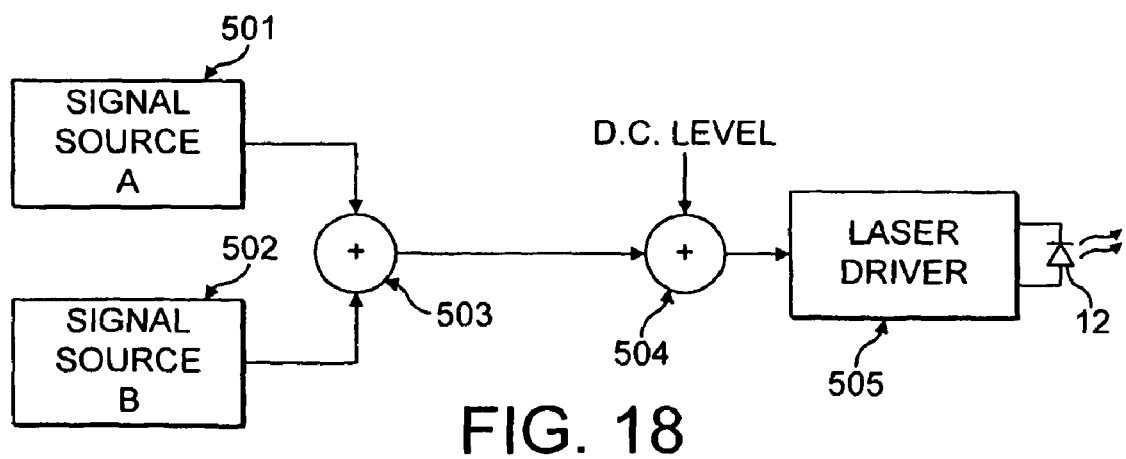
FIG. 18 is a block diagram showing the components of the drive of the laser diode of the open path gas detector.

Referring to FIG. 18, there is shown the basic arrangement of functional blocks employed within the transmitter to drive the laser diode. Of particular note are the two separate signal sources 501 and 502 that are summed by block 503 along with a DC signal 504 to provide a signal that modulates the current through the laser 12. The signal sources are implemented using a direct digital synthesis technique, but any signal generation circuit could be employed.

These two signal sources are used to generate two periodic waveforms, preferably of the same function and amplitude. The frequencies of the two sources differ, typically by a factor greater than 1 up to $10^8$ times, e.g. 1.1 to 100, for example about 10. The waveform function of the two sources is preferably sinusoidal or similar simple waveform, which has the advantage of concentrating information concerning the gas absorption into a relatively small number of frequency components. Other, more complex waveforms can be employed if desired and they allow the gas measurement information to be spread to other frequencies. This may be beneficial in allowing certain noise sources or interfering gas species to be rejected from the analysis of the gas measurement signal FIG. 19 shows the output from two signal sources, A & B, and the resultant signal after they have been summed, C. As the current through the laser is proportional to this signal and the optical wavelength and optical output power of the laser are proportional to current, plot C is also a plot of the current through the laser, as well as its wavelength and optical power output as a function of time.

Figure 1:
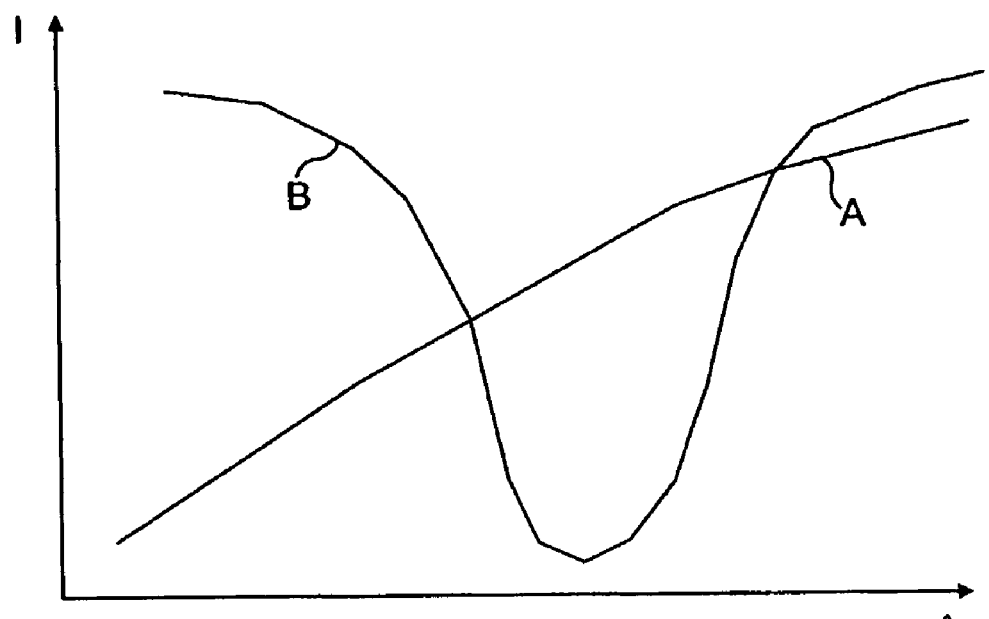
FIGS. 1 and 2 are graphs of the intensity of radiation detected by the detector unit of an open path gas detector.
Figure 2:
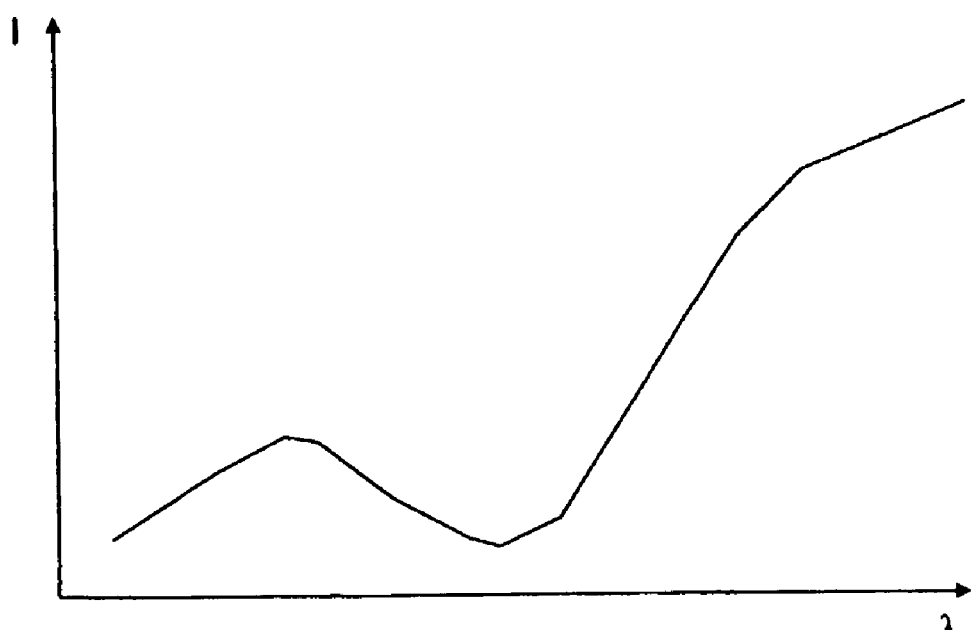

The relationship between the complex modulation waveform C and the gas absorption feature to be measured is illustrated in FIG. 20. Plot H shows the absorption band of a target gas, that is to say the attenuating effect of radiation absorption by the target gas as a function of wavelength; this is the same as plot B of FIG. 1. The average value of waveform C is the DC signal from generator 504 and it is set so that the DC signal gives an output wavelength from the laser that coincides with the peak absorption wavelength of the target gas feature to be measured, which is point I on plot H. The last variable parameter of the modulation waveform, the amplitude of each signal source 501,502, is fixed such that the wavelength of the laser 12 is modulated over a range typically between 2 and 8 times the full width half height (FWHH) of the target gas absorption feature, indicated as J. The wavelength modulation range of each signal source is illustrated on the Figure as K; as shown, K is about 2 times the FWHH.

Figure 21:
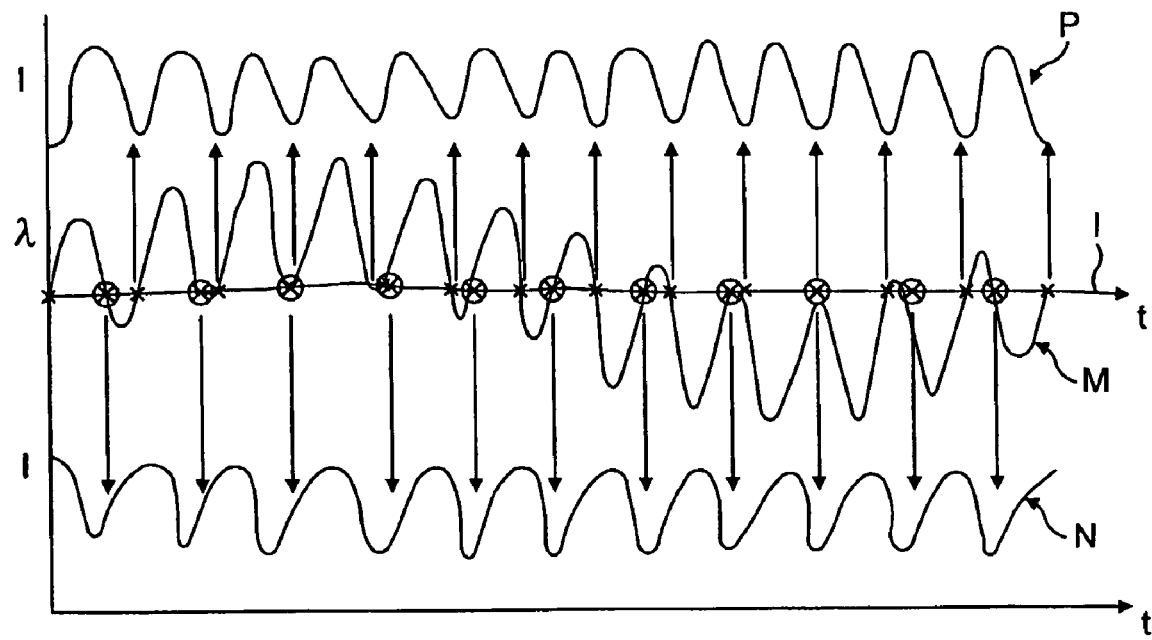
FIG. 21 is a series of three plots, one showing the variation in the wavelength against time of the radiation transmitted across an open path by the gas detector and the other two are plots of the radiation intensity detected at the end of the path showing the component signals resulting from radiation absorption by target gas.

The method by which this complex modulation waveform interacts with the gas absorption, such that information regarding the gas concentration is encoded at frequencies within the signal received by the detector unit 20 can be understood with reference to FIG. 21. This figure shows three plots against time. The centre plot M shows the wavelength modulation of the radiation emitted by the laser with time; the peak absorption of the target gas feature to be detected, i.e. point I of FIG. 20, is shown as the wavelength I. The points on plot M when the wavelength emitted by the laser 12 is at this peak absorption wavelength of the target gas occurs when the wavelength plot is at value I and these points have been marked on plot M with a cross. It can be seen that the separation between adjacent crosses fluctuates and alternate points can be seen to either advance or recede in time with respect to the higher of the two modulation frequencies, shown as plot A of FIG. 19. If one considers only alternate points (for easier understanding the cross of one set of alternate points in plot M has been ringed), it can be seen that the points of each set of alternate points occur at regular intervals.

The frequency between the points of the two sets is related to the frequencies of the two signal sources 501, 502, $F_A$ and $F_B$. The frequency of one set of alternate points is $F_A-F_B$ and the frequency of the other set is $F_A+F_B$.

If there is target gas in the path 30, it will absorb radiation in the target gas absorption band shown in FIG. 20 and consequently there will be a reduction in the amount of radiation reaching the detector 22 and this reduction is related to the amount of target gas in the path. The radiation detected by the detector will be the same as plot C shown in FIG. 19 except it will be reduced at the wavelength of the absorption band of the target gas, which is centred on the midpoint of the band, shown as I in FIG. 20. If one now considers plot M of FIG. 21, the wavelength of the absorption band midpoint wavelength I is shown. The instances of radiation emitted by the laser 12 at wavelength I is, as discussed above, shown by the crosses in FIG. 21 and they can be resolved into two frequencies $F_A-F_B$ and $F_A+F_B$. Thus the absorption of radiation by the target gas occurs in a plot that can be resolved into two plots, one at a frequency of $F_A-F_B$ and the other at a frequency of $F_A+F_B$, which are plots N and P respectively of FIG. 21. The actual gas absorption function will be the sum of these waveforms; however, separation of the two in the figure highlights that the more complex actual signal is primarily made up from two simple periodic waveforms.

A plot of the radiation detected by the detector 22 against time is not shown but will be made up of three components (a) the optical power output of the laser 12, i.e. plot C of FIG. 19, (b) the absorption of the radiation at frequencies $F_A-F_B$ and $F_A+F_B$ due to target gas, as shown in plots N and P in FIG. 21 and (c) absorption by atmospheric conditions. The magnitude of the target gas absorption component (b) will depend on the amount of target gas in the path 30 and if there is no target gas present, the signal detected by the detector will a composite of components (a) and (c) only.

Figure 22:
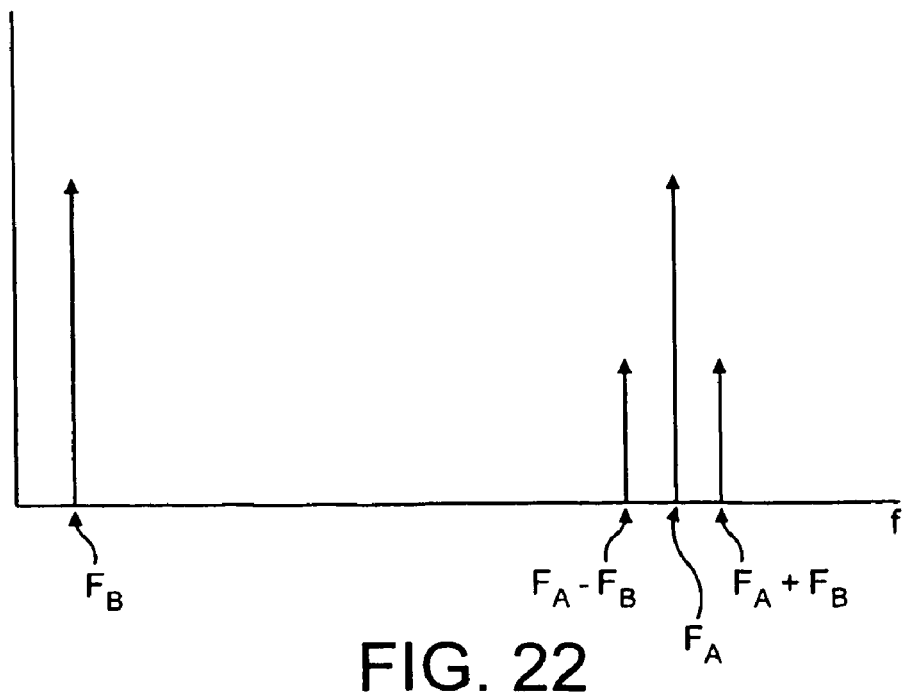
FIG. 22 is a plot showing the frequencies of the radiation detected at the end of the path.

A frequency spectrum of the intensity of the radiation detected can be obtained by a performing a Fourier transform on the detected radiation in the presence of target gas and an example is shown in FIG. 22 where the two base modulation frequencies $F_A$ and $F_B$ and the two primary frequency components $F_A-F_B$ and $F_A+F_B$ that occur in the presence of the gas are evident. Not shown are the higher harmonics of these primary frequencies that will also carry information regarding the presence of gas.

The magnitudes of $F_A-F_B$ and $F_A+F_B$ frequency components are a function of both the gas concentration and numerous atmospheric conditions, which will attenuate the optical signal. To normalise these magnitudes and remove the influence of atmospheric conditions, a quotient ($F_A-F_B/F_A$ and $F_A+F_B/F_A$) can be formed with the magnitude of the $F_A$ frequency component. The magnitude of $F_A$ frequency component is largely unaffected by the presence of gas but is similarly affected by the atmospheric conditions and therefore the quotient is relatively independent of the atmospheric conditions.

With the arrangement described above, it can be seen that the use of two separate signal sources allows the information relating to the strength of the gas absorption to be obtained at frequencies of $F_A-F_B$ and $F_A+F_B$, and the values of these frequencies can be altered by varying either $F_A$ or $F_B$. It is therefore possible to choose of $F_A$ and $F_B$ so that $F_A-F_B$ and $F_A+F_B$ are not harmonics of either of $F_A$ and $F_B$. In this way, the harmonics of neither $F_A$ nor $F_B$ will occur at the target gas detection frequencies of $F_A-F_B$ and $F_A+F_B$.

Figure 23:
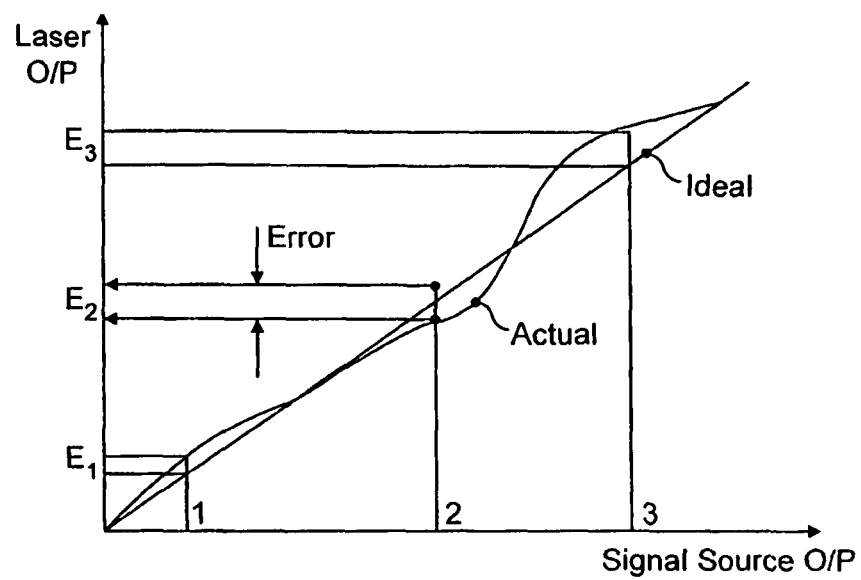
FIG. 23 is a plot of the output from the laser diode against the output of the signal sources of FIG. 18.

The use of a signal obtained from two summed signal sources can provide a different but related advantage. This advantage can be understood by first considering the case of a single source, e.g. 501 or 502, for generating the signal used to drive the laser wavelength scanning. With reference to FIG. 23, each possible output level of the single signal source will result in the laser operating at one specific optical power level and wavelength. The ideal linear relationship between signal source output and the laser output is shown in FIG. 23. The non-linear behaviour of the signal source driving the laser diode 12, which is also shown in FIG. 23, will fluctuate around the plot of the ideal response. The non-linear behaviour results in an error in the output level from the signal source shown in FIG. 23 and consequently an error in the optical power output from the laser. These errors result in a distortion of the waveform of the transmitted optical signal, leading to an error in the gas measurement.

With two signal sources 501,502, the outputs of which are summed, these errors can be reduced, as will now be described.

Any one optical output power level can be obtained from an infinite number of possible combinations of the levels of the two signal sources 501,502. If one considers plot C from FIG. 19, point Y on plot C can be derived by adding together the appropriate levels from plot A and plot B in equal parts. However, point Y could also be derived by adding together plots A and B in unequal parts, e.g. a lesser part of plot A and a greater part of plot B. In theory, the number of signal source levels in plots A and B utilised to derive any point in plot C could approach infinity. If plot C were derived by applying, over time, different proportions of the signals A and B from the two sources 501,502, the average distortion, i.e. error due to the non-linear response, within a period of time at a particular optical output power level will be a function of the average distortion across all signal source level combinations utilised within said period of time, which can reduce the errors shown in FIG. 23. To put it in another way, one can consider the plot of FIG. 23 to be a plot of the output of the laser 12 caused by signal source 501 as a function of the output from signal source 501. When a relatively small proportion of the signal A from signal source 501 is used to generate the laser output signal C, the signal source output will be at level 1, giving rise to a higher laser output than the ideal (error $E_1$). When a larger proportion of the signal A from signal source 501 is used to generate the laser output signal C, the signal source output will be at level 2, giving rise to a lower laser output than the ideal (error $E_2$). Likewise, when a large proportion of the signal A from signal source 501 is used to generate the laser output signal C, the signal source output will be at level 3, giving rise to a higher laser output than the ideal (error $E_3$). Errors $E_1$ to $E_3$ tend to cancel each other out and if an infinite number of values were used, the errors would cancel each other out.

As will be appreciated a relatively small proportion of the signal A from signal source 501 can be used to generate the laser output signal C at signal source output level 1, because a relatively large proportion of signal B from signal source 502 is used at the same time and the two signals are summed. Similar at signal source output level 3 of source 501, a relatively small proportion of signal B from signal source 502 is used. Thus the same considerations will apply to the signal source 502 as described above for signal source 501. By varying the proportions of the signals A and B used to generate a given level in composite signal C rapidly over time, the errors between the actual and ideal plots of FIG. 23 cancel each other out and so the laser output is prone to a much reduced error as compared to the situation in which only one signal source is used.

If, as is preferred, direct digital synthesis is used in sources 501,502 to generate the two signals A and B, only a finite number of different signal source output levels can be generated, and the dual frequency modulation technique described above can therefore only output the same optical power level in a finite number of ways. Such finite values will therefore be used in sequence and eventually the sequence must be repeated. This will limit the improvement in overcoming the errors shown in FIG. 23.

The repetition rate of the sequence, $F_S$, is defined by the repetition rate of the complex modulation waveform, i.e. the number of times the two frequency components (plots A and B) are simultaneously at zero phase each second. Through careful selection of $F_A$ and $F_B$ this repetition rate can be controlled. A practical value for $F_S$ is greater than 1 Hz. The number of times a particular optical power is output within one second is approximately $2 \times F_A$; and therefore the number of times it is output within a particular sequence is:

$2 \times F_A / F_S$.

Given an $F_S$ of 20 Hz and $F_A$ of 50 KHz the number of times a particular optical power will be output per second will be approximately 5000. The reduction in distortion through the use of two signal sources in this case is approximated by the square root of 5000 or a factor of 70.

The limit on the number of different signal source levels imposed by the use of direct digital synthesis also limits the reduction in distortion obtainable. Given the use of a 12-bit DAC for digital synthesis the maximum improvement that could be expected is approximated by the square root of $2^{12}$ or a factor of 64.

Advantages in the electronics used to receive the optical signal transmitted over the open path 30 can also be obtained from the use of the complex modulation waveform C, as described below.

Figure 24:
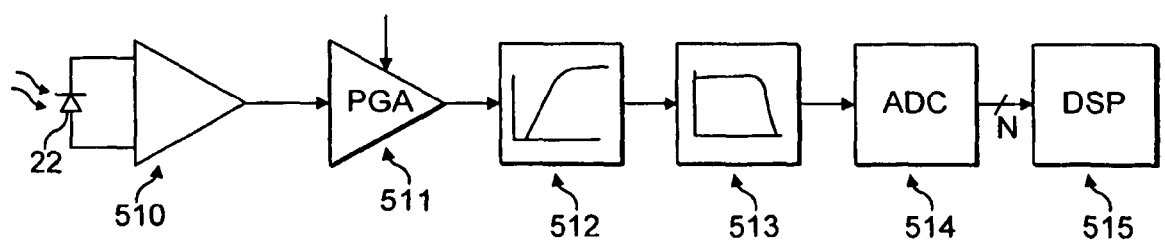
FIG. 24 is a block diagram showing the components of the receiver unit of the open path gas detector.

FIG. 24 shows the basic arrangement of functional blocks within the receiver 20. These include: a photodiode 22 and a trans-impedance amplifier, 510, to convert the received optical power into an electronic signal; a programmable gain amplifier 511, to compensate for variations in atmospheric transmission by boosting the amplification when the signal level is low; a high pass filter 512 and a low pass filter 513 to remove out-of-band signals; and an Analogue to Digital Converter 514 to transform the signal into the digital domain for subsequent processing within a Digital Signal Processor 515.

Except for the high pass filter 512, this arrangement is fairly typical of a known photo-detector electronic system for open path gas detectors. However, if the high pass filter 512 is designed with particular characteristics, the interaction with the complex modulation waveform C, allows the advantage described below to be realised.

If the system is considered initially without the high pass filter 512, all frequency components of the complex modulation would be propagated to the input of the ADC 514. A situation analogous to the transmitter single signal source case described above exists, i.e. one received optical power level is converted to one specific analogue signal level and subsequently converted to one specific digital value. Any non-linear behaviour in the operation of the ADC will result in the analogue signal level being converted to the wrong digital value. This error source results in the digital representation of the signal being distorted compared to the original analogue signal, leading to an error in the gas concentration measurement.

In the early discussion relating to FIG. 22, it was shown the gas concentration in the path could be determined from the magnitude of the $F_A - F_B$, $F_A + F_B$ and $F_A$ frequency components of the received signal. The magnitude of lower $F_B$ modulation frequency is not required and the filtering out of this frequency component from the signal at the input to the ADC using a high pass filter has no effect on the determination of gas concentration in the path.

Figure 25:
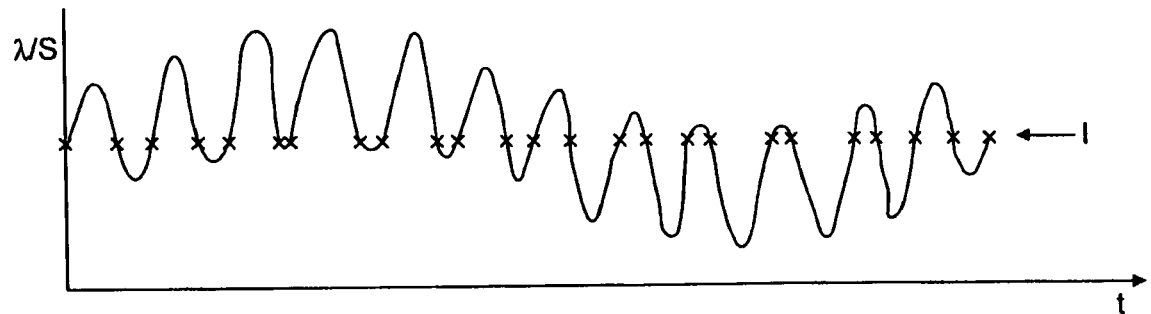
FIG. 25 is a plot of the wavelength of the radiation detected at the end of the path against time, which is also a plot of intensity of the signal detected.
Figure 26:
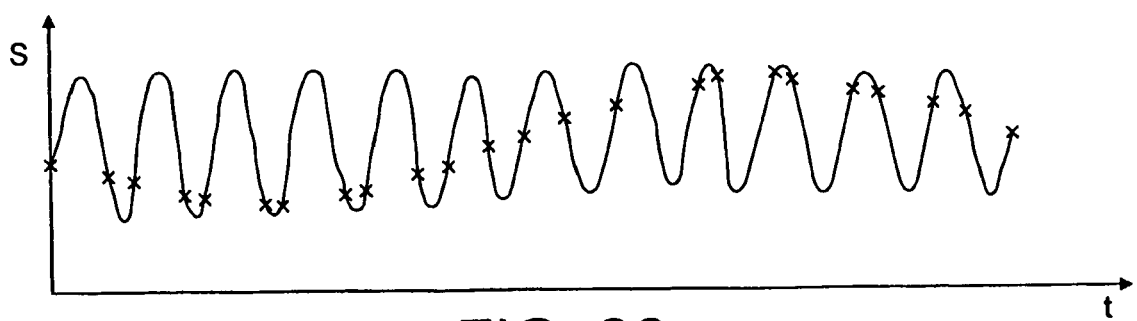
FIG. 26 is a plot of the signal of FIG. 25 after filtering out of one of the frequency components.

The filtering out of the $F_B$ frequency component does however have a dramatic effect upon the form of the signal at the input to the ADC. The effect can be described with reference to FIGS. 25 and 26 The signal detected by the detector 22 is shown in FIG. 25 before filtering out of the $F_B$ frequency and FIG. 26 is the corresponding plot after filtering out of the $F_B$ frequency. Although FIG. 25 is a plot of optical power (signal intensity) against time, it could equally be a plot of wavelength against time since the power emitted by the diode 12 varies in step with the wavelength emitted.

The signals in FIGS. 25 and 26 are shown without any target gas being present in the path 30. However if target gas were to be present in the path 30, the signal would be reduced at the points where the wavelength is at the absorption wavelength of the target gas (wavelength I shown in FIG. 25) and these points are shown with crosses in FIG. 25. As described earlier in connection with FIG. 21, the points vary with frequencies $F_A - F_B$ and $F_A + F_B$ and so if target gas is present, there is a signal at $F_A - F_B$ and $F_A + F_B$ that is proportional to the amount of gas in the path.

When the low $F_B$ frequency is filtered out, the signal is as shown in FIG. 26; the crossed points of FIG. 25 indicating the wavelength I (target gas absorption wavelength) are transformed in FIG. 26 so that they cycle between minimum and maximum signal level at a frequency of $F_B$. Consequently, one wavelength of light and therefore one optical power level is no longer represented by a single electrical signal level where it always has the same distortion but rather by the full range of possible values over a period of time. The average distortion, over a period of time, that is introduced by the conversion to a digital value of a received optical power level will therefore be a function of the average of the distortion of all signal levels utilised to represent the optical power level over said period of time; in the same way as was described above in relation to the non-linear relationship between the signal sources 501,502 and the output from the laser 12 the overall error will be less than that generally arising at the various individual signal levels.

The presence of target gas will still give rise to signals at frequencies of $F_A - F_B$ and $F_A + F_B$, as described even after filtering out of $F_B$, and therefore the filtering has no effect on the gas measurement at frequencies of $F_A - F_B$ and $F_A + F_B$ described above, except to reduce the errors arising from the non-linear behaviour of the various electronic components, particularly the ADC. Likewise, the filtering will not affect the value of $F_A$, which is used to form the quotient $F_A - F_B / F_A$ and/or $F_A + F_B / F_A$ used in the measurement of target gas In theory, the number of signal levels utilised could approach infinity, reducing the distortion to zero; however, as with the signal source case detailed above, the number is finite; dependant upon the number of times the same optical power level is present before the sequence is repeated and the number of different signal levels discernable by the Analogue to Digital Converter.

The repetition rate of the sequence, $F_S$, and the number of times the same optical power level is present, $2 \times F_A / F_S$, is as defined for the dual signal source case above. Similarly, given an $F_S$ of 20 Hz and $F_A$ of 50 KHz the number of times a particular optical power will be present will be approximately 5000, giving a reduction in distortion of a factor of about 70.

The above described arrangement of a dual signal sources in the transmitter, a high pass filter 512 proceeding the analogue to digital converter 514 in the receiver and the dual frequency modulation schema of waveform C, allows a level of performance to be achieved that is beyond that that would be expected from a given set of electronic components.

These performance gains allow the measurement of lower gas concentrations than would otherwise be possible using digital synthesis of the modulation waveforms and early conversion of received optical signal into the digital domain, thereby allowing processing of the signal and the determination of the gas concentration using digital processing methods; they also reduce the use of analogue processing steps which are inherently more sensitive to variation in temperature, drift with passage of time, and which are more expensive for a given level of performance.

Although the invention has been described in terms of the frequencies of the looped steering path of the transmitted radiation (30) and of any variations in this path caused by mechanical vibrations at the transmitter, it is preferred to use high frequency sidebands of the gas sensing modulation frequency, which will typically be about 50 kHz, to determine the magnitude of these components. This technique is well known in other fields, for example simple AM radio where the sound signal is superimposed as sidebands on the high frequency carrier signal.

The invention claimed is:

1. An open path gas detector comprising:
a transmitter unit having
a radiation transmitter;
optics configured to shape radiation emitted by the transmitter into a beam for transmission along a path, at least a partial alignment shadow is formed in the beam;
a communications signal detector; and
a receiving unit having
a detector configured to detect the beam of radiation from the transmitter unit; and
a communications transmitter configured to send a data signal to the transmitter unit at a communications wavelength that is different from a transmitted wavelength, the data signal containing data concerning the intensity of radiation detected by the detector, and where the optics is arranged to direct the data signal towards the communications signal detector;
where the transmitter unit includes
a signal generator configured to generate a composite signal having at least two different modulation frequency components;
a driver arranged to drive the radiation transmitter with the composite signal to generate radiation that changes wavelength in accordance with the composite signal;
wherein the signal generator is so configured that at least one of the following:
a) the sum of any two modulation frequency components in the composite signal or harmonics thereof and
b) the difference between any two modulation frequency components in the composite signal or harmonics thereof
is neither at the fundamental frequency of any of the modulation frequency components of the composite signal nor at a harmonic thereof.

2. A detector as in claim 1 which includes a controller configured to detect when the beam is aligned with the receiving unit and to steer a radiation deflector, the controller is arranged to monitor the detector to detect the alignment shadow and to steer the radiation deflector so that the shadow impinges on the detector.

3. A detector as in claim 1 wherein:
the transmitter unit includes an optical element configured to direct radiation emitted by the transmitter towards the optics,
the communications signal detector is located on the side of the optical element remote from the optics, and
the optical element is capable of transmitting the data signal at the communications wavelength to the communications signal detector.

4. A detector as in claim 3 where the optical element comprises one of a reflector or a refractor.

5. A detector as in claim 4 where the reflector comprises a mirror that is one of transparent or translucent at the communications wavelength and is reflective at the wavelength transmitted by the radiation transmitter.

6. A detector as in claim 3 where the optical element is steerable to direct radiation emitted by the radiation transmitter along a desired path.

7. A detector as in claim 3 where the communications signal detector has a field of view in the range of at least ±0.1°-±0.5°.

8. A detector as in claim 3 where the transmitter emits amplitude modulated radiation which at least in part, is transmitted along the path.

9. A detector as in claim 5 which includes a radiation deflector and a plurality of electromechanical elements, supporting the radiation deflector, where the electromechanical elements change position in accordance with a signal applied to them, whereby the radiation deflector can be steered to direct the radiation along a desired path.

10. A detector as in claim 9 where each of the elements comprises a strip having two opposed ends and a central part located between the ends, where the strip is anchored at each of its ends and the radiation deflector is movably supported on the central part of the strips, and wherein the electromechanical elements have a resonance frequency in a range of at least 150 Hz, –500 Hz.

11. A detector as in claim 1 where the:
radiation transmitter comprises a tuneable laser diode, capable of emitting radiation at a wavelength absorbed by the target gas, and where the transmitter unit further includes a radiation deflector, having a deflecting part and a non-deflecting part both the deflecting part and the non-deflecting part are located in a path of the radiation emitted by the transmitter and wherein the non-deflecting part either does not deflect the radiation emitted by the transmitter or, does so to a different extent than the deflecting part.

12. A detector as in claim 11 where the radiation deflector comprises a steerable mirror having a reflective surface for reflecting radiation emitted by the transmitter.

13. A detector as in claim 11 where the transmitter unit further includes:
a container that is translucent to radiation in the wavelength range emitted by the transmitter, the container being arranged in the path of radiation that has passed through the non-deflecting part and configured to contain a sample of a material that absorbs radiation in at least part of a wavelength range emitted by the transmitter, the material preferably being the target gas,
a radiation detector arranged to detect the radiation that has passed through the container and to generate a signal in accordance with the intensity of such radiation, and
a controller configured to control the wavelength of the radiation emitted by the radiation transmitter to maintain it within a pre-determined range with respect to the radiation absorbed by the sample.

14. A detector as in claim 11 where the optics include at least one element having a surface facing the radiation deflector and arranged to reflect radiation from the radiation deflector and focus it so that it passes through the non-deflecting part of the radiation deflector, and a sensor configured to receive the radiation reflected by the surface and to generate a signal indicative of at least one of the intensity or wavelength of the radiation emitted by the transmitter.

15. A detector as in claim 13 which includes a second radiation deflector arranged to deflect radiation that has passed through the non-deflective part of the first radiation deflector towards the container, and where the non-deflecting part of the first radiation deflector forms a shadow in the beam of radiation reflected by a surface and where the second deflector is arranged in the shadow.

16. A detector as in claim 1 where the detector includes:

a filter configured to remove one or more of the frequency components from the detected radiation signal;

a signal processor having an input arranged to receive a filtered signal from the filter and providing a non-linear output, the processor is selected from a class which includes an analogue to digital converter, or, an amplifier, configured to provide an output indicative of the filtered signal; and a second processor configured to process the filtered signal output to detect absorption of the radiation at a predetermined wavelength.

* * * * *